(12) United States Patent
Cantat et al.

(10) Patent No.: US 10,189,868 B2
(45) Date of Patent: Jan. 29, 2019

(54) METHOD FOR DEPOLYMERISING OXYGENATED POLYMER MATERIALS

(71) Applicant: Commissariat a l'Energie Atomique et aux Energies Alternatives, Paris (FR)

(72) Inventors: Thibault Cantat, Issy les Moulineaux (FR); Elias Feghali, Montrouge (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 15/535,533

(22) PCT Filed: Dec. 16, 2015

(86) PCT No.: PCT/IB2015/059684
§ 371 (c)(1),
(2) Date: Jun. 13, 2017

(87) PCT Pub. No.: WO2016/098021
PCT Pub. Date: Jun. 23, 2016

(65) Prior Publication Data
US 2017/0349613 A1    Dec. 7, 2017

(30) Foreign Application Priority Data
Dec. 17, 2014   (FR) ..................... 14 62581

(51) Int. Cl.
| C07F 7/18 | (2006.01) |
| C07C 1/213 | (2006.01) |
| C07C 1/22 | (2006.01) |
| C07C 29/09 | (2006.01) |
| C08J 11/18 | (2006.01) |

(52) U.S. Cl.
CPC ............ *C07F 7/1804* (2013.01); *C07C 1/213* (2013.01); *C07C 1/22* (2013.01); *C07C 29/09* (2013.01); *C08J 11/18* (2013.01); *C07C 2531/02* (2013.01); *C07C 2531/14* (2013.01); *C08J 2367/00* (2013.01); *C08J 2369/00* (2013.01); *C08J 2397/00* (2013.01); *Y02W 30/706* (2015.05)

(58) Field of Classification Search
None
See application file for complete search history.

(56) References Cited

PUBLICATIONS

Krall et al., "Controlled hydrogenative depolymerization of polyesters and polycarbonates catalyzed by ruthenium(II) PNN pincer complexes," Chemical Communications, 50: 4884-4887 (2014).
Nunes et al., "PET depolymerisation in supercritical ethanol catalysed by [Bmim][BF4]," RSC Advances, 4: 20308-20316 (2014).
International Search Report issued in corresponding International Patent Application No. PCT/IB2015/059684 dated Feb. 17, 2016.

*Primary Examiner* — Clinton A Brooks
(74) *Attorney, Agent, or Firm* — Morgan, Lewis & Bockius LLP

(57) ABSTRACT

The present invention concerns a method for depolymerizing oxygenated polymer materials and the use of said method in the recycling of plastic materials and the preparation of aromatic compounds that can be used as fuel, synthesis intermediates and raw materials in the construction sectors and in the petrochemical, electrical, electronic, textile, aeronautical, pharmaceutical, cosmetics and agrochemical industries. The present invention also concerns the use of aromatic compounds obtained by the method for depolymerizing oxygenated polymer materials according to the invention, in the production of fuels, electronic components, plastic polymers, rubber, drugs, vitamins, cosmetic products, perfumes, food products, synthetic threads and fibers, synthetic leathers, glues, pesticides and fertilizers.

21 Claims, 4 Drawing Sheets

METHOD FOR DEPOLYMERISING OXYGENATED POLYMER MATERIALS

The present invention relates to a process for depolymerizing oxygenated polymer materials and to the use of said process in the recycling of plastics and to the preparation of aromatic compounds that can be used as fuel, synthetic intermediates, raw materials in the sectors of construction and in the petrochemical, electrical, electronic, textile, aeronautical, pharmaceutical, cosmetic and agrochemical industries.

The present invention also relates to the use of aromatic compounds obtained via the process for depolymerizing oxygenated polymer materials according to the invention, in the manufacture of fuels, electronic components, plastic polymers, rubber, medicaments, vitamins, cosmetic products, fragrances, food products, synthetic yarns and fibers, synthetic leathers, adhesives, pesticides and fertilizers.

Oxygenated polymers are currently base constituents of a large proportion of materials of everyday life and in particular plastics. Specifically, a plastic consists essentially of a polymer, which, after mold and forming operations, leads to the production of a finished or semifinished object. These plastics generally have high molecular masses and are often derived from petrochemistry, but plastics of natural origin exist. Nowadays, increasing interest has been shown in plastics on account of their ease of manufacture, their relatively low cost and also their versatility. However, the relatively high cost of recycling these materials using the current processes poses economic problems requiring new solutions that can function in concert with the changes in legislation. Thus, the recycling of materials containing oxygenated polymers has become a major challenge of contemporary society.

Several recycling methods have been developed to address this problem. Among these methods, chemical recycling (or tertiary recycling) is a recycling method that complies with the principles of sustainable development. Specifically, this type of recycling makes it possible to recover petrochemical constituents, polymeric waste materials and plastic waste materials and to use them as precursors in the creation of products with high added value. Polymer materials may thus be considered as a source of carbon-based materials (S. M. Al-Salem, P. Lettieri, J. Baeyens, *Progress in Energy and Combustion Science*, 2010, 36 (2010) pages 103-129: S. H. Park and S. H. Kim, *Fashion and Textiles*, 2014, 1, pages 1-17).

Chemical recycling methods are generally divided into two categories: those which regenerate the starting monomers or oligomers and those which generate other types of molecules that have applications in fine chemistry or as fuel. Many chemical recycling methods exist in the literature (D. S. Achilias, D. A. Louka, G. Tsintzou, I. A. Koutsidis, I. Tsagkalias, L. Andriotis, N. P. Nianias, P. Siafaka, *Recent Advances in the Chemical Recycling of Polymers (PP, PS, LDPE, HDPE, PVC, PC, Nylon, PMMA)*, INTECH Open Access Publisher, 2012, ISBN: 953510327X, 9789535103271).

However, chemical recycling or tertiary recycling methods have non neglictible operating drawbacks such as execution of the reaction at high temperature and at high pressures and also the use of metals to catalyze the reactions. Furthermore, methods that can simultaneously recycle several types of polymeric resins (recycling of copolymers or of polymer mixtures) and which are resistant to the additives present in the materials are rare.

Thus, there is a real need to develop an alternative method to the already-existing methods for the tertiary recycling of polymer materials, in particular of oxygenated polymer materials, into compounds with high added value, which overcomes the drawbacks of the tertiary recycling methods of the prior art.

In particular, there is thus a real need to develop a depolymerization process which can be applied to the recycling of polymer materials, in particular of oxygenated polymer materials, into compounds with high added value.

More particularly, there is a real need for a process for depolymerizing polymer materials, in particular oxygenated polymer materials:

which leads to the formation of less oxygenated compounds having a higher energy content;
which is environmentally friendly:
which can be performed under mild and industrially advantageous operating conditions;
which avoids the use of catalysts based on polluting and expensive metals;
which is efficient, the efficiency being reflected by good conversion or even total conversion of the oxygenated polymer material into chemical compounds with good purity (at least 90 mol % relative to the total number of mols of compounds obtained) or which can be readily purified;
with good selectivity relative to the chemical compounds obtained;
which has selectivity that can be modulated and adapted as a function of the chemical compound(s) that it is desired to prepare;
which allows selective cleavage of certain bonds of the oxygenated polymer material;
which is general and versatile, being able to be adapted to any type of oxygenated polymer material to be depolymerized; and/or
which is capable of resisting the additives that may be present in the oxygenated polymer materials to be depolymerized.

The aim of the present invention is, precisely, to satisfy at least these needs by providing a process for depolymerizing oxygenated polymer materials by selective cleavage of the oxygen-carbonyl bonds of the ester functions (—CO—O—) and of the carbonate functions (—O—CO—O—), characterized in that it comprises a step of placing said oxygenated polymer materials in contact with a silane compound of formula (I)

in which
R$^1$, R$^2$ and R$^3$ represent, independently of each other, a hydrogen atom, a halogen atom, a hydroxyl group, an alkyl group, an alkenyl group, an alkynyl group, an alkoxy group, an aryloxy group, a silyl group, a siloxy group, an aryl group, an amino group, said alkyl, alkenyl, alkynyl, alkoxy, silyl, siloxy, aryl and amino groups being optionally substituted, or
R$^1$ is as defined above and R$^2$ and R$^3$, taken together with the silicon atom to which they are linked, form an optionally substituted silyl heterocycle;
in the presence of a catalyst.

For the purposes of the invention, an oxygenated polymer material is a material comprising at least one oxygenated polymer and optionally at least one additive. The amount of oxygenated polymer(s) and the amount and nature of the additives present in the oxygenated polymer material vary as a function of the polymer material and of the targeted applications. However, in the context of the invention, at least 50% by mass of the oxygenated polymer material is oxygenated polymer.

In the context of the present invention, an oxygenated polymer denotes a polymer or copolymer in which the repeating units of the main chain contain the ester function (—CO—O—), also known as polyesters, or the carbonate function (—O—CO—O—) also known as poly carbonates.

The oxygenated polymers of the invention are mainly synthetic or semisynthetic polymers, but may also be biosourced polymers, i.e. polymers derived from animal or plant biomass. The additive(s) that may be present in the material may be introduced before or during the forming of the material, to give or improve one (or occasionally several) specific properties. Examples of additives that may be mentioned include stabilizers, antioxidants, colorants, pigments, wetting agents, dispersants, emulsifiers, thickeners, biocides, plasticizers, photoprotective agents, etc.

The process of the invention has the advantage of withstanding the presence of additive(s) in the polymer materials. No problem of catalyst poisoning could be observed with the additives commonly used in polymer materials. Specifically, the greatest challenge of recycling is not limited to the depolymerization of the polymer present alone in the reaction medium (pure polymer), but also extends to its depolymerization in a commercial material that may contain additives such as colorants, mineral fillers, antioxidants, etc. The presence of these additives in the material may deactivate the catalyst used for performing the depolymerization, and thus render the reaction inefficient. The process of the invention is thus of great industrial interest since it is capable of withstanding the additives and/or impurities present in the starting polymer material, which, for example, may be plastic waste material.

The process for depolymerizing oxygenated polymer materials according to the invention is represented schematically in FIG. 1.

The oxygenated polymer materials of the invention may be an oxygenated polymer, or a mixture of oxygenated polymers, or a mixture of at least two polymers, at least one of which is an oxygenated polymer for the purposes of the invention, optionally with one or more additives.

Preferably, the oxygenated materials of the invention comprise one or more additives.

When the oxygenated polymer is a copolymer, the main chain of said copolymer may comprise repeating units containing one or more ester functions (—CO—O—) and/or one or more carbonate functions (—O—CO—O—) and optionally repeating units chosen from ethylenic, propylenic and vinyl units, vinyl units substituted with one or more chlorine or fluorine atoms, and styrene, styrene-butadiene, acrylic and methacrylic units.

In the rest of the description, the term "polymer" may also denote a "copolymer". Thus the term "polymer" may cover homopolymers (a polymer derived from only one monomer species) and copolymers (a polymer derived from at least two different monomers).

The synthetic or semisynthetic oxygenated polymers of the invention may be chosen from:
saturated or unsaturated polyesters chosen, for example, from polyglycolic acid (PGA), polylactic acid (PLA), polycaprolactone (PCL), polyhydroxyalkanoate (PHA), polyhydroxybutyrate (P3HB), polyhydroxyvalerate (PHV), polyethylene adipate (PEA), polybutylene succinate (PBS), poly(3-hydroxybutyrate-co-3-hydroxyvalerate (PHBV), polyethylene terephthalate (PET), polybutylene terephthalate (PBT), polytrimethylene terephthalate (PTT), polyethylene naphthalate (PEN), polycarbonates chosen, for example, from PC-BPA, polypropylene carbonate (PPC), polyethylene carbonate (PEC), poly(hexamethylene carbonate), allyl diglycol carbonate (ADC) or CR-39.

Among the oxygenated polymers, polyethylene terephthalate (PET), polylactic acid (PLA) and polycarbonate (PC-BPA) are the ones most extensively studied in the literature since their recycling is advantageous in several respects:

Polyethylene terephthalate (PET) is one of the plastics most commonly used worldwide due to its lightness, its durability, its chemical resistance and also its low cost.

Polylactic acid (PLA) is very advantageous from an environmental viewpoint since it is mainly derived from renewable sources, such as maize, potato and other agricultural products (but is in competition with nutrition here). On account of its biodegradability combined with its mechanical strength and its transparency, PLA is considered as a green and sustainable material that may be seen as a promising alternative to petroleum-based polymer resins, especially PET.

Polycarbonates (PC-BPA) are thermoplastics with excellent mechanical properties and great impact strength, UV resistance and also excellent electrical resistance. Consequently, polycarbonates are used in a wide variety of applications, such as compact disks, armored windows, food packagings or carbonated drink bottles.

In the context of the invention, biosourced oxygenated polymers are more particularly those derived from plant biomass in which the aromatic units are linked via ester bonds. In this respect, mention may be made of hydrolyzable tannins, especially gallotannins and ellagitannins, and suberin.

The depolymerization process of the invention for certain oxygenated polymer materials is represented in FIG. 2.

The oxygenated polymers are advantageously chosen from
polyesters, especially PET and PLA;
polycarbonates, especially PC-BPA; and/or
hydrolyzable tannins, especially gallotannins and ellagitannins, and suberin.

As already indicated, the materials of the invention may be a mixture of at least two polymers, at least one of which is an oxygenated polymer within the meaning of the invention. In this case, the other polymer(s) present in the material may be chosen from polyolefins, especially polyethylene and polypropylene; polyvinyl acetyl (PVAC), polyvinyl alcohol (PVAL); polystyrene (PS), acrylonitrile butadiene styrene (ABS); styrene-butadiene (SBR); acrylonitrile styrene acrylate (ASA); saturated or crosslinked polyurethanes; polymethyl methacrylate (PMMA), polyacrylonitrile (PAN); polyvinyl chloride (PVC), polyvinylidene chloride (PVDC); polytetrafluoroethylene (PTFE), polyvinyl fluoride (PVF), polyvinylidene fluoride (PVDF), ethylene tetrafluoroethylene (ETFE), perfluoroalkoxy (PFA); polyether ether ketone (PEEK); styrene-butadiene-styrene (SBS) block copolymers; polyamides such as PA6, PA 12 and PA 6.6;

polyurethanes; polyureas; copolymers of polyureas and of polyurethanes (known under the names Spandex, Lycra or elastane).

The process for depolymerizing the oxygenated polymer materials according to the invention gives chemical compounds which may contain siloxy groups and which have a smaller number of carbons than that of the oxygenated polymer(s) present in the starting material. The compounds obtained may lead, after hydrolysis, to chemical compounds with an average molar mass of less than 600 g/mol.

The hydrolysis of chemical compounds containing siloxy groups derived from the depolymerization may lead to the corresponding hydroxylated compounds, which, in turn, may lead to the corresponding deoxygenated compounds by using the reductive hydrosilylation conditions described in this process.

The depolymerization process according to the invention may lead to the formation of chemical compounds in gaseous form such as methane, ethane or propane, in liquid form such as para-xylene or ethylene glycol and/or in solid form such as bisphenol A (BPA).

In the case of the depolymerization of natural oxygenated polymers, the depolymerization products may be monocyclic (for example in the case of gallotannin), mono-, bi- and/or tricyclic (for example in the case of ellagitannin) and optionally mono-, di-, and/or trioxygenated aromatic compounds. The depolymerization may also generate saturated or unsaturated nonaromatic molecules, consisting of carbon and hydrogen atoms which may optionally be mono-, di-, and/or trioxygenated.

Depending on the nature of the starting material used, the nature of the hydrosilane and its amount, the catalyst used and the reaction time, the nature of the depolymerization product may change. Thus, by varying the operating conditions used, one type of product may be selectively obtained.

Specifically, one of the advantages of the process of the invention is the possibility of selectively obtaining a variety of chemical compounds from the same type of polymer by controlling the operating conditions. For example, in the case of PET, the depolymerization process may lead to the production of 1,4-phenylenedimethanol and ethylene glycol, or alternatively ethane and para-xylene.

In the context of the present invention, the selectivity is related to the nature of the products formed and also to the nature of the bonds cleaved.

The bonds targeted and selectively cleaved by the depolymerization process of the invention are the oxygen-carbonyl bonds of ester functions (—CO—O—) and of carbonate functions (—O—CO—O). Thus, the C—O bonds of functionalities in which the carbon atom is linked to another carbon atom via an sp or $sp^2$ multiple bond (for example C=C—O) are not cleaved during the depolymerization process of the invention. For example, the aryl ethers present in polyphenols are not cleaved. C—C single, double and triple bonds are not cleaved either via the depolymerization process of the invention. For example, polystyrene (PS) and polyvinyl chloride (PVC) are not depolymerized by the process of the invention.

Depending on the operating conditions, during the depolymerization process, the carbonyl function —C=O may be reduced to a silyl ether —CH—OSiR$^1$R$^2$R$^3$ in which R$^1$, R$^2$, and R$^3$ are as defined in the context of the present invention. The operating conditions may also be chosen so as to continue the reduction of the silyl ether by breaking its C—O bond, so as to further deoxygenate the molecule to a methylene function —CH$_2$—.

The depolymerization process of the invention is of great versatility especially with respect to the types of starting oxygenated polymer materials.

Moreover, by carefully controlling the operating conditions, the depolymerization of a polymer material comprising a mixture of polyester(s) and/or of polycarbonate(s) may be selective. Without wishing to be bound by theory, the difference in reactivity of the oxygen-carbonyl bonds of an ester function and of a carbonate function may promote the selective cleavage of one of these functions over the other. Furthermore, the electronic effect (for example the inductive effects linked to the polarizations of a σ bond and the mesomeric effects due to the delocalization of the π electrons) and the steric hindrance of the substituents close to the oxygen-carbonyl bond may have an impact on the reactivity of the bond to be cleaved. For example, in the case of a material comprising a PC-BPA+PLA mixture or of a material comprising a PET+PLA mixture, PC-BPA and PET are selectively cleaved.

Moreover, the depolymerization step of the process of the invention is performed under mild conditions (i.e. low temperatures and pressures) and makes it possible to dispense with harsh temperature and pressure reaction conditions conventionally used, for example, in the recycling of polymer materials.

Moreover, the yield of chemical compounds with an average molar mass of less than 600 g/mol obtained by the depolymerization process and after the hydrolysis step depends on the starting polymer material and also on the operating conditions applied. The yield is generally good (from 30 to 99 mol % relative to the total number of mols of monomer units present in the polymer(s) of the starting material. By approximation, and in order to calculate the molar yield of the depolymerization process, the starting polymer material is considered to be exclusively formed from the polymer studied.

The yield is calculated by applying the following formula:

$$\text{Yield} = n(\text{molecules})/n(\text{monomer units})$$

n (molecules) being the number of mols of a given molecule with an average molar mass of less than 600 g/mol obtained after depolymerization, and n (monomer units) being the total number of mols of monomer units present in the polymers initially introduced. It should be noted that the number of monomer units is different from the number of bonds that can be cleaved. The quantification is made relative to the number of mols of units in the polymer that can potentially give simple molecules (with an average molar mass of less than 600 g/mol). After the depolymerization, these units are referred to as "monomer units present in the polymers".

For the purposes of the present invention, the term "alkyl" means a linear, branched or cyclic, saturated, optionally substituted carbon-based radical, comprising 1 to 12 carbon atoms, preferably 1 to 8 carbon atoms. Examples of saturated, linear or branched alkyls that may be mentioned include methyl, ethyl, propyl, butyl, pentyl, hexyl, octyl, nonyl, decyl, undecyl and dodecyl radicals and the branched isomers thereof. Cyclic alkyls that may be mentioned include cyclopropyl, cyclobutyl, cyclopentyl, cyclohexyl, bicyclo[2,1,1]hexyl and bicyclo[2,2,1]heptyl radicals. Examples of cyclic alkyls bearing unsaturation that may be mentioned include cyclopentenyl and cyclohexenyl.

The term "alkenyl" or "alkynyl" means a linear, branched or cyclic, optionally substituted, unsaturated carbon-based radical, said unsaturated carbon-based radical comprising 2 to 12 carbon atoms, preferably 2 to 8 carbon atoms, comprising at least one double bond (alkenyl) or one triple bond (alkynyl). In this respect, examples that may be mentioned include ethylenyl, propylenyl, butenyl, pentenyl, hexenyl, acetylenyl, propynyl, butynyl, pentynyl and hexynyl radicals and the branched isomers thereof.

For the purposes of the invention, the alkyl, alkenyl and alkynyl groups may be optionally substituted with one or more hydroxyl groups; one or more alkoxy groups; one or more siloxy groups; one or more halogen atoms chosen from fluorine, chlorine, bromine and iodine atoms; one or more nitro groups (—NO$_2$); one or more nitrile groups (—CN); one or more aryl groups; with the alkoxy, siloxy and aryl groups as defined in the context of the present invention.

The term "aryl" generally denotes a cyclic aromatic substituent comprising from 6 to 20 and preferably from 6 to 12 carbon atoms. In the context of the invention, the aryl group may be monocyclic or polycyclic. As a guide, mention may be made of phenyl, benzyl and naphthyl groups. The aryl group may be optionally substituted with one or more hydroxyl groups, one or more alkoxy groups, one or more siloxy groups, one or more halogen atoms chosen from fluorine, chlorine, bromine and iodine, one or more nitro groups (—NO$_2$), one or more nitrile groups (—CN), one or more alkyl groups, with the alkoxy, siloxy and alkyl groups as defined in the context of the present invention.

The term "heteroaryl" generally denotes a monocyclic or polycyclic aromatic substituent comprising from 5 to 10 members, preferably from 5 to 7 members, including at least 2 carbon atoms, and at least one heteroatom chosen from nitrogen, oxygen, boron, silicon, phosphorus and sulfur. The heteroaryl group may be monocyclic or polycyclic. As a guide, mention may be made of furyl, benzofuryl, pyrrolyl, indolyl, isoindolyl, azaindolyl, thiophenyl, benzothiophenyl, pyridyl, quinolyl, isoquinolyl, imidazolyl, benzimidazolyl, pyrazolyl, oxazolyl, isoxazolyl, benzoxazolyl, thiazolyl, benzothiazolyl, isothiazolyl, pyridazinyl, pyrimidinyl, pyrazinyl, triazinyl, cinnolinyl, phthalazinyl and quinazolinyl groups. The heteroaryl group may be optionally substituted with one or more hydroxyl groups, one or more alkoxy groups, one or more halogen atoms chosen from fluorine, chlorine, bromine and iodine atoms, one or more nitro groups (—NO$_2$), one or more nitrile groups (—CN), one or more aryl groups, one or more alkyl groups, with the alkyl, alkoxy and aryl groups as defined in the context of the present invention.

The term "alkoxy" means an alkyl, alkenyl or alkynyl group, as defined above, linked to an oxygen atom (—O-alkyl, O-alkenyl, O-alkynyl).

The term "aryloxy" means an aryl group as defined above, linked via an oxygen atom (—O-aryl).

The term "heterocycle" generally denotes a monocyclic or polycyclic substituent, comprising from 5 to 10 members, preferably from 5 to 7 members, which is saturated or unsaturated, containing from 1 to 4 heteroatoms chosen, independently of each other, from nitrogen, oxygen, boron, silicon, phosphorus and sulfur. As a guide, mention may be made of morpholinyl, piperidyl, piperazinyl, pyrrolidinyl, imidazolidinyl, imidazolinyl, pyrazolidinyl, tetrahydrofuryl, tetrahydropyranyl, thianyl, oxazolidinyl, isoxazolidinyl, thiazolidinyl and isothiazolidinyl substituents. The heterocycle may be optionally substituted with one or more hydroxyl groups, one or more alkoxy groups, one or more aryl groups, one or more halogen atoms chosen from fluorine, chlorine, bromine and iodine, one or more nitro groups (—NO$_2$), one or more nitrile groups (—CN), one or more alkyl groups, with the alkyl, alkoxy and aryl groups as defined in the context of the present invention.

The term "halogen atom" means an atom chosen from fluorine, chlorine, bromine and iodine atoms.

The term "silyl" group means a group of formula [—Si(X)$_3$] in which each X, independently of each other, is chosen from a hydrogen atom; one or more halogen atoms chosen from fluorine, chlorine, bromine and iodine; one or more alkyl groups; one or more alkoxy groups; one or more aryl groups; one or more siloxy groups; with the alkyl, alkoxy, aryl and siloxy groups as defined in the context of the present invention. When at least one of the X represents several siloxy groups, said siloxy groups may be repeated several times so as to lead to polymeric organosilanes of general formula

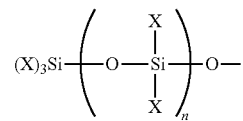

in which X is as defined above and n is an integer between 1 and 20 000, advantageously between 1 and 5000, more advantageously between 1 and 1000. In this respect, examples that may be mentioned include the monovalent radicals of polydimethylsiloxane (PDMS), of polymethylhydroxysiloxane (PMHS) and of tetramethyldisiloxane (TMDS) as represented below by structural formulae:

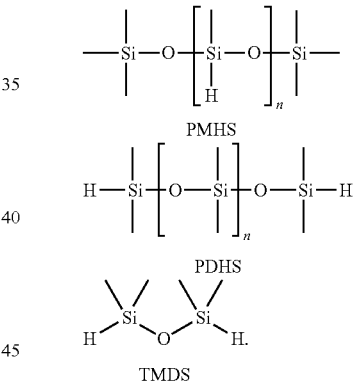

The term "siloxy" group means a silyl group as defined above, linked via an oxygen atom (—O—Si(X)$_3$) with X as defined above.

For the purposes of the invention, the term "silyl heterocycle" means a monocyclic or polycyclic substituent, comprising from 5 to 15 members, preferably from 5 to 7 members, which is saturated or unsaturated, containing at least one silicon atom and optionally at least one other heteroatom chosen from nitrogen, oxygen and sulfur. Said silyl heterocycle may be optionally substituted with one or more hydroxyl groups; one or more alkyl groups, one or more alkoxy groups; one or more halogen atoms chosen from fluorine, chlorine, bromine and iodine atoms; one or more aryl groups, with the alkyl, alkoxy and aryl groups as defined in the context of the present invention. Among the silyl heterocycles, examples that may be mentioned include 1-silacyclo-3-pentene or 1-methyl-1,1-dihydrido-2,3,4,5-tetraphenyl-1-silacyclopentadiene as represented below:

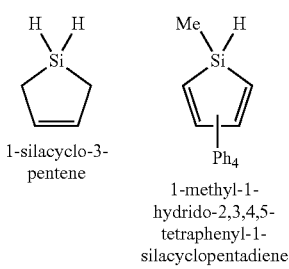

1-silacyclo-3-pentene 1-methyl-1-hydrido-2,3,4,5-tetraphenyl-1-silacyclopentadiene Among the silyl heterocycles, examples that may also be mentioned include methyl siloxane, 1-phenyl-1-silacyclohexane, 1-silabicyclo[2.2.1]heptane, 1-methyl-1-silacyclopentane and 9,9-dihydro-5-silafluorene corresponding to the following structural formulae:

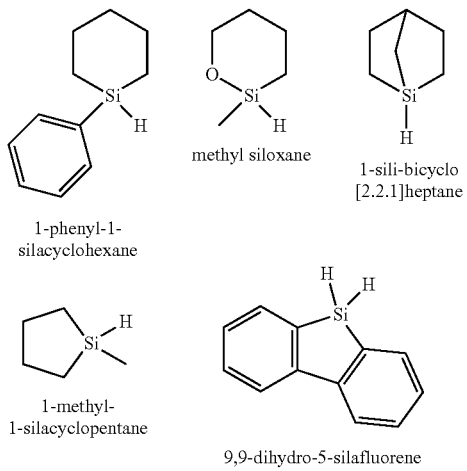

1-phenyl-1-silacyclohexane methyl siloxane 1-sili-bicyclo[2.2.1]heptane 1-methyl-1-silacyclopentane 9,9-dihydro-5-silafluorene The term "polyol" means an organic compound characterized by the presence of a certain number of hydroxyl (—OH) groups. In the context of this invention, a polyol compound contains at least two hydroxyl groups. More precisely, the term "polyol" means a compound of formula Y—(OH)$_m$, in which m is greater than or equal to 1, and Y is chosen from one or more alkyl groups, one or more alkoxy groups, one or more siloxy groups, one or more aryl groups, one or more heteroaryl groups, with the alkyl, alkoxy, siloxy, aryl and heteroaryl groups as defined in the context of the present invention.

The term "amino" group means a group of formula —NR$^4$R$^5$, in which:

R$^4$ and R$^5$ represent, independently of each other, a hydrogen atom, an alkyl group, an alkenyl group, an alkynyl group, an aryl group, a heteroaryl group, a heterocycle, a silyl group, a siloxy group, with the alkyl, alkenyl, alkynyl, aryl, heteroaryl, heterocycle, silyl and siloxy groups as defined in the context of the present invention; or R$^4$ and R$^5$, taken together with the nitrogen atom to which they are attached, form a heterocycle optionally substituted with one or more hydroxyl groups; one or more alkyl groups; one or more alkoxy groups; one or more halogen atoms chosen from fluorine, chlorine, bromine and iodine atoms; one or more nitro groups (—NO$_2$); one or more nitrile groups (—CN); one or more aryl groups; with the alkyl, alkoxy and aryl groups as defined in the context of the present invention.

In the context of the invention, "suberin" denotes a biosourced polymer mainly found in higher plants. This waxy organic substance is impermeable and is found on the cellulose-based walls of certain plant cells, in particular those of cork, of which it constitutes the main constituent. Suberin contains two domains: the polyaliphatic domain and the polyaromatic domain essentially formed from hydroxycinnamic acid derivatives. The exact composition of suberin varies as a function of the species. A representation of the structure of suberin is shown in FIG. 3.

The term "tannin" denotes a biosourced polymer contained in many plants. This organic substance may be contained, for example, in the leaves (sumac), the bark and the wood (e.g. oak, acacia) and/or the roots (badan) of plants. This amorphous polyphenolic compound is especially used in the tanning of hides to make leather, the manufacture of inks or in pharmacology. There are three major categories of tannins: hydrolyzable tannins, non-hydrolyzable or condensed tannins, and phlorotannins. This definition encompasses pseudo-tannins which are tannins of low molecular weight associated with other compounds.

For the purposes of the invention, the term "hydrolyzable tannins" means compounds consisting of mixtures of polygalloyl glucoses (these are polymers of molecules formed from gallic acid derivatives and β-D-glucose, for instance in the case of tannic acid) and/or poly-galloyl derivatives of quinic acid containing between 3 and 12 gallic acid units per molecule. These compounds contain essentially ester bonds linking the aromatic units to a polyol, which facilitates its hydrolysis with weak acids or bases.

The term "gallotannins" means hydrolyzable tannins derived from gallic acid, in which the gallic acid is linked via ester bonds to a central polyol. In these compounds, the galloyl units may similarly undergo oxidative cross couplings or esterification reactions. Several types of gallotannins exist, which are essentially distributed according to their chemical composition, for instance: galloyl glucoses (these are molecules formed from a bond between gallic acid and β-D-glucose), galloyl quinic acids, galloyl shikimic acids. FIG. 4 is a representation of the structure of tannic acid, also known as β-1,2,2,3,6-pentagalloyl-O-D-glucose and belonging to the category of gallotannins.

For the purposes of the invention, the term "ellagitannin" means gallotannins or galloyl groups which have undergone oxidative C—C coupling. This intramolecular coupling takes place for the majority of plants between the carbon atoms: C2 and C3 or alternatively between C4 and C6. This type of polyphenol generally forms macrocycles, whereas this is not observable with gallotannins.

For the purposes of the invention, the term "catalyst" means any compound that is capable of modifying, especially by increasing, the rate of the chemical reaction in which it participates, and which is regenerated at the end of the reaction. This definition encompasses not only catalysts, i.e. compounds which exert their catalytic activity without the need to undergo any modification or conversion, but also compounds (also known as precatalysts) which are introduced into the reaction medium and which are converted therein into a catalyst. In the process of the invention, the catalyst is an organic or organometallic molecule, i.e. it may or may not contain metal ions or transition elements. However, organic catalysts have the advantage of being able to set aside the toxicity problems generally observed for metal catalysts and also cost problems associated with the use of precious metals.

It is in particular necessary for the catalyst to be chosen taking into account especially its steric hindrance, its ability to activate the silane compound and its solubility in the reaction medium.

The catalyst may be an organic catalyst chosen from:

the carbocations of formula $(X^1)_3C^+$ with $X^1$ representing a hydrogen atom, an alkyl group, an aryl group, an alkoxy group, a silyl group, a siloxy group and a halogen atom, as defined above, said carbocations being chosen from the trityl cation $((C_6H_5)_3C^+)$, tropilium $(C_7H_7)^+$, the benzylic cation $(C_6H_5CH_2^+)$, the allylic cation $(CH_3—CH^+—CH=CH_2)$, methylium $(CH_3^+)$, cyclopropylium $(C_3H_5^+)$, the cyclopropyl carbocation of formula $C_3H_5—C^+R^1R^2$ with $R^1$ and $R^2$ as defined above, said cyclopropyl carbocation being chosen from the dimethylcyclopropyl carbocation and the dicyclopropyl carbocation, the triazabicyclodecene (TBD) cation, acylium $(R^1—C=O)^+$ with $R^1$ as defined above and chosen from methyl, propyl and benzyl, benzenium $(C_6H_5)^+$, and the norbornyl cation $(C_7H_{11})^+$;

oxoniums chosen from $(CH_3)_3O^+BF_4^-$ (Meerwein's reagent) and $(CH_3CH_2)_3O^+BF_4^-$;

a silylium ion $(R^5)_3Si^+$ with $R^5$ as defined previously, for example chosen from $Et_3Si^+$ and $Me_3Si^+$;

disilyl cations, preferably disilyl cations containing a bridging hydride chosen from the formulae indicated below

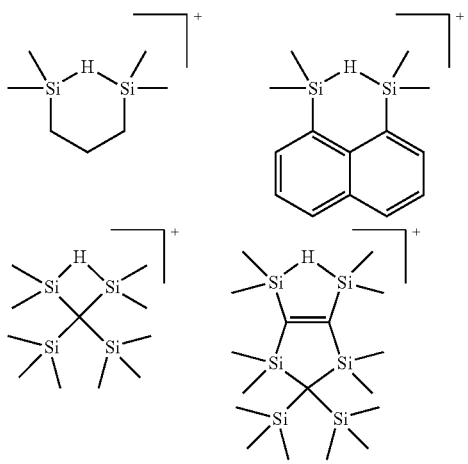

The carbocations mentioned above are commercial or may be readily synthesized by a person skilled in the art via various synthetic processes, for example: the cation pool process, the internal redox process, the process using a leaving group, processes using Lewis or Bronsted acids. These processes are described in the following references: R. R. Naredla and D. A. Klumpp, *Chem. Rev.* 2013, 113, pages 6905-6948: M. Saunders and H. A. Jimenez-Vazquez, *Chem. Rev.* 1991, 91, pages 375-397.

It should be noted that the anionic counterion of the silylium ion, of the carbocations and of the disilyl cations mentioned above is preferably a halide chosen from $F^-$, $Cl^-$, $Br^-$ and $I^-$, or an anion chosen from $BF_4^-$, $SbF_6^-$, $B(C_6F_5)_4^-$, $B(C_6H_5)_4^-$, $TfO^-$ or $CF_3SO_3^-$, $PF_6^-$.

The organic catalyst may preferably be triphenylcarbenium tetrakis(perfluorophenyl)borate $[(Ph)_3C^+B(C_6F_5)_4]^-$.

In the process of the invention, the catalyst may also be organometallic. As examples of organometallic catalysts, mention will be made of the iridium complexes corresponding to formula (II) represented below, in which $R^6$ represents an alkyl or aryl group as defined previously, and preferably a tert-butyl group;

$R^7$ represents a hydrogen atom or an alkyl group as defined previously, and preferably a hydrogen atom;

$X^2$ represents a $—CH_2—$ group or an oxygen atom, and preferably an oxygen atom;

$Y^-$ represents a counterion chosen from $B(C_6F_5)_4^-$, and $B(C_6H_5)_4$, and preferably $B(C_6F_5)_4^-$; and S represents a solvent molecule, coordinated to the complex, chosen from dimethyl sulfoxide (DMSO), acetonitrile ($CH_3CN$) and acetone ($CH_3COCH_3$), and preferably acetone.

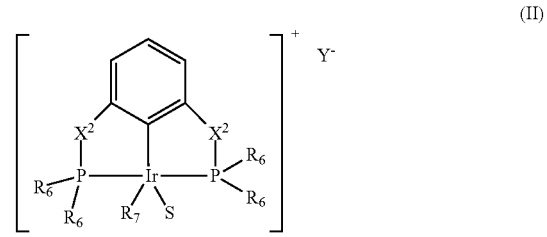

Preferably, the iridium catalyst is $[(POCOP)Ir(H)(acetone)]^+B(C_6F_5)_4^-$ with (POCOP) representing 2,6-bis(di-tert-butylphosphinito)phenyl. This catalyst may be prepared according to the processes described by I. Gottker-Schnetmann, P. White, and M. Brookhart, *J. Am. Chem. Soc.* 2004, 126, pages 1804-1811: and by J. Yang and M. Brookhart, *J. Am. Chem. Soc.* 2007, 129, pages 12 656-12 657.

In the process of the invention, the catalyst may also be organometallic. In this respect, mention may be made of the ruthenium complexes corresponding to formula (III) below:

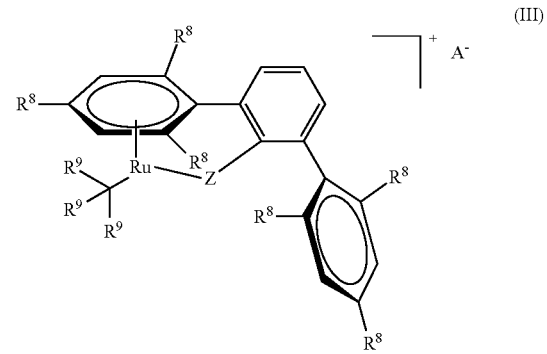

in which $R^8$ represents a hydrogen atom or an alkyl group as defined previously, $R^8$ preferably being a methyl group;

$R^9$ represents an aryl or an alkyl group as defined previously, said aryl and alkyl groups being optionally substituted, $R^9$ preferably being $p-FC_6H_4$;

Z represents a $—CH_2—$ group, an oxygen atom or a sulfur atom, Z preferably being a sulfur atom; and $A^-$ represents a counterion chosen from $B(C_6F_5)_4^-$ and $[CHB_{11}H_5Cl_6]^-$, $A^-$ preferably being $B(C_6F_5)_4^-$.

This type of catalyst may be prepared according to the processes described by T. Stahl, H. F. T. Klare, and M. Oestreich, *J. Am. Chem. Soc.*, 2013, 135, pages 1248-1251.

The catalyst may also be of Lewis acid type chosen from:
- the boron compounds of formula $B(X^3)_3$ with $X^3$ representing a hydrogen atom, an alkyl group, an aryl group, an alkoxy group as defined previously, said boron compounds being chosen from $BF_3$, $BF_3(Et_2O)$, $BCl_3$, $BBr_3$, triphenylhydroborane, tricyclohexylhydroborane, $B(C_6F_5)_3$, B-methoxy-9-borabicyclo[3.3.1]nonane (B-methoxy-9-BBN), B-benzyl-9-borabicyclo[3.3.1]nonane (B-benzyl-9-BBN);
- the borenium compounds $R^{10}R^{11}B^+$ with $R^{10}$ and $R^{11}$ representing, independently of each other, a hydrogen atom, a halogen atom, a hydroxyl group, an alkyl group, an alkenyl group, an alkynyl group, an alkoxy group, an aryloxy group, a silyl group, a siloxy group, an aryl group, an amino group, said alkyl, alkenyl, alkynyl, alkoxy, silyl, siloxy, aryl and amino groups being optionally substituted. The borenium compounds in which $R^{10}=R^{11}=$ phenyl and $R^{10}=R^{11}=$ methylene are examples the preparation of which is described (Y. Shoji, N. Tanaka, K. Mikami, M. Uchiyama and T. Fukushima, Nat. Chem., 2014, 6, 498-503). Said borenium compounds are, for example, Me-TBD-BBN$^+$, the borenium ferrocene derivatives corresponding to formula

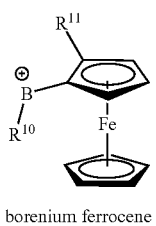

borenium ferrocene in which $R^{10}$ and $R^{11}$ are as defined previously, for example $R^{10}=$phenyl and $R^{11}=$ 3,5-dimethylpyridyl (J. Chen, R. A. Lalancettea and F. Jäkle, *Chem. Commun.*, 2013, 49, pages 4893-4895);
- the aluminum compounds chosen from $AlCl_3$, $AlBr_3$, aluminum isopropoxide $Al(O-i-Pr)_3$, aluminum ethoxide $(Al(C_2H_3O_2))$, the Krossing salt $[Ag(CH_2Cl_2)]\{Al[OC(CF_3)_3]_4\}$, $Li\{Al[OC(CF_3)_3]_4\}$, the cationic aluminum compounds of formula $(X^4)_2Al^+$ with $X^4$ being a halogen atom, an alkoxy group, an alkyl group as defined previously, for instance $Et_2Al^+$;
- indium compounds chosen from $InCl_3$, $In(OTf)_3$;
- iron compounds chosen from $FeCl_3$, $Fe(OTf)_3$;
- tin compounds chosen from $SnCl_4$, $Sn(OTf)_2$;
- phosphorus compounds chosen from $PCl_3$, $PCl_5$, $POCl_3$;
- trifluoromethanesulfonate or triflate compounds $(CF_3SO_3^-)$ of transition metals and of lanthanides chosen from scandium triflate, ytterbium triflate, yttrium triflate, cerium triflate, samarium triflate and neodymium triflate.

In the context of the present invention, OTf represents the triflate or trifluoromethanesulfonate ion of formula $CF_3SO_3^-$; the terms triflate and trifluoromethanesulfonate, OTf or $CF_3SO_3^-$ may thus be used indiscriminantly to denote the same species.

The preparation of the borenium ferrocene derivatives is described by J. Chen, R. A. Lalancettea and F. Jäkle, *Chem. Commun.*, 2013, 49, pages 4893-4895; the preparation of the Krossing salts is described by I. Krossing, *Chem.-Eur. J.*, 2001, 7, page 490; and the preparation of $Et_2Al^+$ is described by M. Khandelwal and R. J. Wehmschulte, *Angew. Chem. Int. Ed.* 2012, 51, pages 7323-7326.

The catalyst of Lewis acid type is preferably chosen from $BF_3$; $InCl_3$; the borenium ferrocene derivative as defined previously in which $R^{10}=$ phenyl and $R^{11}=$ 3,5-dimethylpyridyl.

The catalysts may, where appropriate, be immobilized on heterogeneous supports so as to ensure easy separation of said catalyst and/or recycling thereof. Said heterogeneous supports may be chosen from supports based on silica gel and plastic polymers, for instance polystyrene; carbon-based supports chosen from carbon nanotubes; silicon carbide; alumina, and magnesium chloride ($MgCl_2$).

Some of the abbreviations used in the context of the invention are represented below:

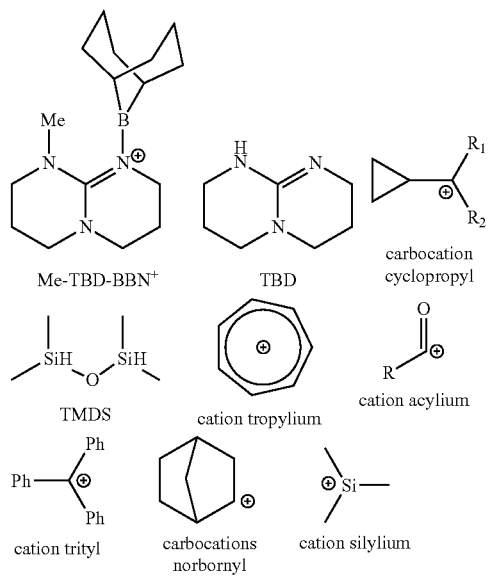

According to a particular embodiment of the invention, the depolymerization process uses a silane compound of formula (I) in which $R^1$, $R^2$ and $R^3$ represent, independently of each other, a hydrogen atom, a hydroxyl group; an alkyl group chosen from methyl, ethyl, propyl, butyl, and branched isomers thereof; an alkoxy group whose alkyl radical is chosen from methyl, ethyl, propyl, butyl and branched isomers thereof; an aryl group chosen from phenyl and benzyl; an aryloxy group whose aryl radical is chosen from phenyl and benzyl; a siloxy group ($—O—Si(X)_3$) in which each X, independently of each other, is chosen from a hydrogen atom, an alkyl group chosen from methyl, ethyl, propyl, an aryl group chosen from phenyl and benzyl, a polymeric organosilane of general formula

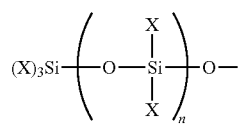

in which X is as defined above and n is an integer between 1 and 20 000, advantageously between 1 and 5000, more advantageously between 1 and 1000; said alkyl, alkoxy, aryl, aryloxy, siloxy and aryl groups being optionally substituted.

According to another particular embodiment of the invention, the depolymerization process uses a silane compound of formula (I) in which $R^1$, $R^2$ and $R^3$ represent, independently of each other, a hydroxyl group; an alkyl group chosen from methyl, ethyl, propyl, butyl, and branched isomers thereof; an alkoxy group in which the alkyl radical is chosen from methyl, ethyl, propyl, butyl and branched isomers thereof; an aryl group chosen from phenyl and benzyl; an aryloxy group in which the aryl radical is chosen from phenyl and benzyl; a siloxy group (—O—Si(X)$_3$) in which each X, independently of each other, is chosen from a hydrogen atom, an alkyl group chosen from methyl, ethyl, propyl, an aryl group chosen from phenyl and benzyl, a polymeric organosilane of general formula

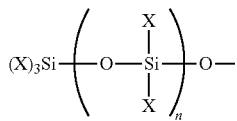

in which X is as defined above and n is an integer between 1 and 20 000, advantageously between 1 and 5000, more advantageously between 1 and 1000; said alkyl, alkoxy, aryl, aryloxy, siloxy and aryl groups being optionally substituted.

In a particular embodiment of the invention, the depolymerization process uses a silane compound of formula (I) in which $R^1$, $R^2$ and $R^3$ represent, independently of each other, a hydrogen atom; an alkyl group chosen from methyl, ethyl, propyl and the branched isomer thereof; an aryl group chosen from benzyl and phenyl; a siloxy group chosen from polydimethylsiloxane (PDMS), polymethylhydroxysiloxane (PMHS) and tetramethyldisiloxane (TMDS).

In another particular embodiment of the invention, the depolymerization process uses a silane compound of formula (I) in which $R^1$, $R^2$ and $R^3$ represent, independently of each other, an alkyl group chosen from methyl, ethyl, propyl and the branched isomer thereof; an aryl group chosen from benzyl and phenyl; a siloxy group chosen from polydimethylsiloxane (PDMS), polymethylhydroxysiloxane (PMHS) and tetramethyldisiloxane (TMDS).

PMHS and TMDS, which are two byproducts of the silicone industry, may be upgraded in the depolymerization process according to the invention. The use of two industrial byproducts for creating molecules with high added value is economically very advantageous.

As already indicated, the depolymerization process is performed under very mild operating conditions; low temperature and pressure, relatively short reaction time. Total conversion of the starting reagent(s) may be obtained within a few minutes to a few hours. It should be noted that the conversion is expressed relative to the oxygenated polymer material.

In the process according to the invention, the depolymerization may be performed under a pressure of one or of a mixture of inert gas(es) chosen from nitrogen and argon, or of gases generated by the process, especially methane and hydrogen. The pressure may be between 0.2 and 50 bar, preferably between 0.2 and 30 bar, more preferentially between 1 and 20 bar, limits inclusive.

The depolymerization may be performed at a temperature of between 0 and 150° C., preferably between 0 and 125° C., more preferentially between 25 and 70° C., limits inclusive.

The reaction time depends on the degree of conversion of the silane compound of formula (I), on the nature of the starting polymer material and also on the desired degree of silylation in the targeted final compounds.

The depolymerization may be performed within a time from 1 minute to 200 hours, advantageously from 1 minute to 48 hours, preferably from 10 minutes to 48 hours, limits inclusive.

The depolymerization, in particular the reaction between the various reagents, may take place in one or a mixture of at least two solvents chosen from:
 silyl ethers, preferably chosen from 1,1,1,3,3,3-hexamethyldisiloxane ((Me$_3$Si)$_2$O), 1,1,1,3,3,3-hexaethyldisiloxane ((Et$_3$Si)$_2$O);
 hydrocarbons, preferably chosen from benzene, toluene, pentane and hexane;
 sulfoxides, preferably chosen from dimethyl sulfoxide (DMSO);
 alkyl halides, preferably chosen from chloroform, methylene chloride, chlorobenzene, dichlorobenzene.

The silanes of formula (I) and the catalysts used in the depolymerization step are generally commercial compounds or may be prepared via the processes known to those skilled in the art.

The mole ratio between the silane compound of formula (I) and the starting polymer material depends on the type of starting polymer material used (type of polymer material and the amount of additives and of contaminants present in said polymer material) and on the type of final compounds desired (production of siloxy functions (—O—SiR$^1$R$^2$R$^3$) in the final product or total reduction down to the deoxygenated derivative). Specifically, since the depolymerization process of the invention cleaves the sp3 carbon-oxygen bonds, the silyl bonds (—C—O—Si—) may be readily reduced to a —C—H bond. The selectivity relative to the type of final compounds will depend on the number of equivalence of silane compound of formula (I) added.

Thus, in the context of the present invention, the mol ratio between the silane compound of formula (I) and the oxygenated polymer material may be between 0.1 and 20, preferably between 0.5 and 10, limits inclusive.

The amount of catalyst used in the depolymerization process may be from 0.001 to 1 molar equivalent, preferably from 0.001 to 0.9 equivalent by mass, more preferentially from 0.01 to 0.7 molar equivalent, even more preferentially from 0.01 to 0.5 molar equivalent, limits inclusive, relative to the initial number of mols of the starting oxygenated polymer material.

After the depolymerization, the resulting compounds may be in silyl form. A simple hydrolysis under conditions that are well known to those skilled in the art may then lead to the corresponding aromatic compounds in their non-silyl forms.

In the context of the present invention, the term "hydrolysis" means a process for transforming the siloxy groups present in silyl compounds derived from depolymerization of lignin, into hydroxyl groups, via a desilylation reaction. This transformation may be performed under acidic or basic conditions or alternatively in the presence of fluoride ions, these conditions being well known to those skilled in the art. In the context of the present invention, the hydrolysis process is preferably chosen from: 2 M HCl or H$_2$SO$_4$ in THF; 10% NaOH or KOH in a water/THF mixture; TBAF.3H$_2$O in THF; commercial solution of TBAF (1M) in THF.

A simple filtration makes it possible to recover the optionally supported catalyst and to remove any byproducts.

The process of the invention allows the preparation of compounds comprising one or more siloxy functions (—OSiR$^1$R$^2$R$^3$) or of compounds free of oxygen atoms. In the case where the starting oxygenated polymer material comprises several cleavable functions, the depolymerization will then lead to a monosiloxane or polysiloxane, which, after the hydrolysis, will lead to the production of a simple alcohol or of a polyol. The compounds derived from the depolymerization are obtained in good purity, i.e. a purity of greater than or equal to 90 mol %, preferably between 90 and 99.9 mol %. The molar purity may be determined by spectroscopic or chromatographic analysis, for example by proton NMR ($^1$H NMR) or gas chromatography coupled to mass spectrometry (GC-MS). Specifically, in the process of the invention, the compounds formed may be readily purified via separation techniques that are well known to those skilled in the art and conventionally used in this field, for instance column chromatography, distillation for the volatile products, etc. Since the compounds obtained are generally small molecules i.e. molecules with a molar mass of less than 600 g/mol, their separation from the side products that may have formed, which are generally oligomers with bonds that cannot be cleaved by the process of the invention, is easy taking into account the very different physicochemical properties of oligomers and of the compounds obtained.

The process of the invention is very robust since it withstands the contaminants that may be present in the commercial polymer materials (such as traces of waters and traces of metals) and also additives such as colorants, added to the polymer materials, for instance plastics.

The process of the invention may be used for the recycling of composite materials such as resins containing PVC and PET and which are difficult to recycle. Specifically, the ester bonds of PET are cleaved whereas the C—C bonds of PVC remain intact.

This process may provide a solution to waste storage by making it possible to recycle the mixture of PET and PLA waste materials. Specifically, given their resemblance as regards the physical and visual properties, plastics (PET) and bioplastics (PLA) are commonly mixed. However, their separation is very expensive and the current recycling processes do not make it possible to recycle the two polymers at the same time. A real problem thus exists for the recycling of mixtures of plastics (PET) and of bioplastics (PLA). The process of the invention makes it possible to recycle a mixture of PET and of PLA either by selectively cleaving PET or by cleaving PET and PLA, as a function of the chosen operating conditions.

Thus, one subject of the invention is the use of the depolymerization process of the invention for the recycling of plastic materials containing at least one oxygenated polymer within the meaning of the invention. In particular, a subject of the invention is the use of the process of the invention for the recycling of plastics or of mixtures of plastics containing at least one oxygenated polymer, i.e. a polymer or copolymer whose main chain comprises ester and/or carbonate functions, for instance PLA, PET, PC-BPA.

A subject of the invention is also a process for recycling plastic materials or mixtures of plastic materials containing at least one oxygenated polymer within the meaning of the invention, i.e. a polymer or copolymer whose main chain comprises ester and/or carbonate functions, for instance PLA, PET, PC-BPA, said process comprising a step of depolymerizing oxygenated polymer materials according to the invention.

In the recycling process, the step of depolymerizing oxygenated polymer materials according to the invention may be preceded by a step of preparing or of transforming said plastic materials. By way of example, a step of milling, extrusion, spraying or micronization may be used so as to increase the surface area of the materials and to improve the performance qualities of the depolymerization step according to the invention.

On conclusion of the depolymerization process of the invention and after hydrolysis, aromatic compounds with a molecular weight of less than 600 g/mol, for instance benzene, toluene, xylenes (BTX), substituted coniferols, phenol, aromatic polyols, quinines, catechol derivatives and hydroxycatechol may be obtained when the starting oxygenated polymer material contains aromatic units. These compounds may be used as fuel, synthetic intermediates, raw materials in the fields of construction, in the petrochemical industry, in the electrical industry, in the electronics industry, in the textile industry, in the aeronautical industry, in the pharmaceutical industry, in the cosmetic industry or in the agrochemical industry.

The process for recycling plastic materials or mixtures of plastic materials may optionally be followed by a step of chemical transformation or of physical forming of the depolymerization products provided by the present process. By way of example, the silyl products obtained by depolymerization of oxygenated polymer materials may be hydrolyzed in the presence of fluoride anions to give alcohols.

One subject of the invention is thus a process for preparing mono-, di- and/or tricyclic aromatic compounds in which each ring may optionally be mono-, di- and/or trioxygenated, comprising a step of depolymerizing oxygenated polymer materials according to the process of the invention. In this process, after the step of depolymerizing oxygenated polymer materials according to the invention, a hydrolysis step may optionally prove to be necessary.

Optionally, the process for preparing mono-, di- and/or tricyclic aromatic compounds in which each ring may optionally be mono-, di- and/or trioxygenated may be followed by a step of chemical transformation or of physical forming of the depolymerization products provided by the process of the invention. By way of example, the aromatic silyl products obtained by depolymerizing oxygenated polymer materials may be hydrolyzed in the presence of fluoride anions to give the corresponding aromatic alcohols.

A subject of the invention is also the use of mono-, di- and/or tricyclic aromatic compounds in which each ring may optionally be mono-, di- and/or trioxygenated, obtained via the process for depolymerizing oxygenated polymer materials according to the invention, in the manufacture of fuels, electronic components, plastic polymers, rubber, medicaments, vitamins, cosmetic products fragrances, food products, synthetic yarns and fibers, synthetic leathers, adhesives, pesticides and fertilizers.

Other advantages and characteristics of the present invention will emerge on reading the examples below, which are given as nonlimiting illustrations, and of the attached figures, in which:

FIG. 1 represents the process for depolymerizing the oxygenated polymer materials according to the invention. A and B represent two identical or different groups chosen from one or more optionally substituted alkyl groups, one or more optionally substituted alkenyl groups, one or more optionally substituted alkynyl groups, one or more optionally substituted aryl groups, one or more optionally substituted heteroaryl groups, with the alkyl, alkenyl, alkynyl, aryl and heteroaryl groups as defined in the context of the present invention. n is an integer between 1 and 20 000.

EXAMPLES

Figure 1:
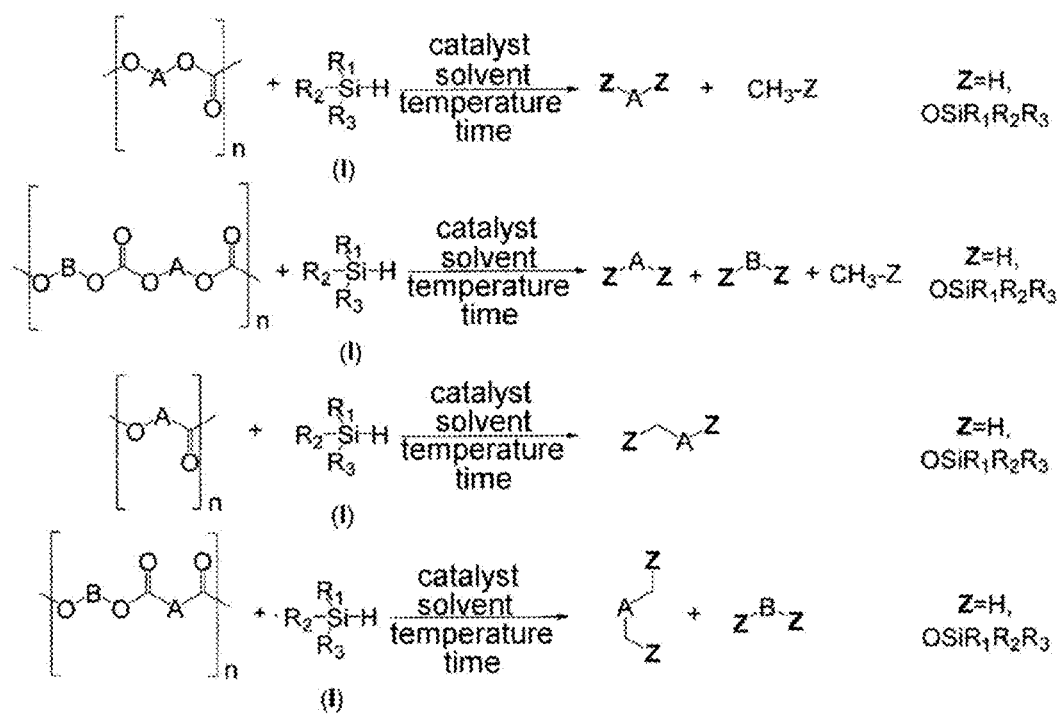
Figure 2:
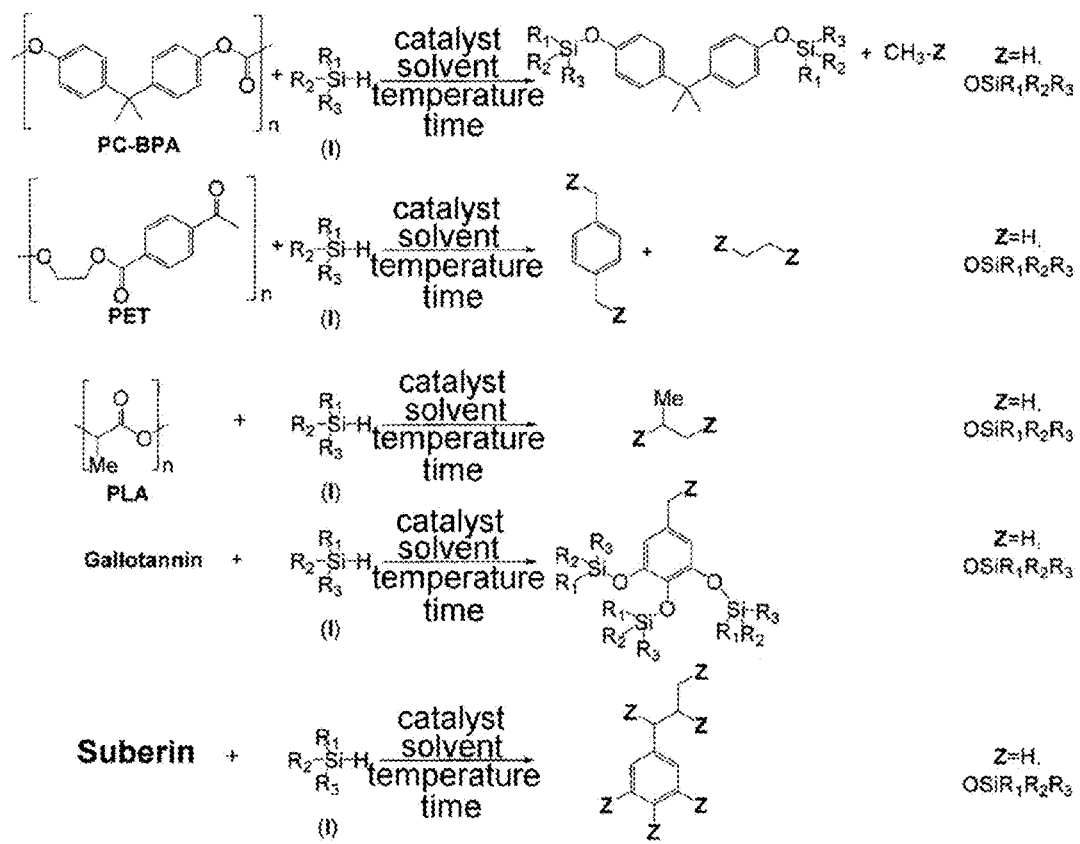
FIG. 2 represents the process of depolymerization of the invention for a few oxygenated polymer materials.
Figure 3:
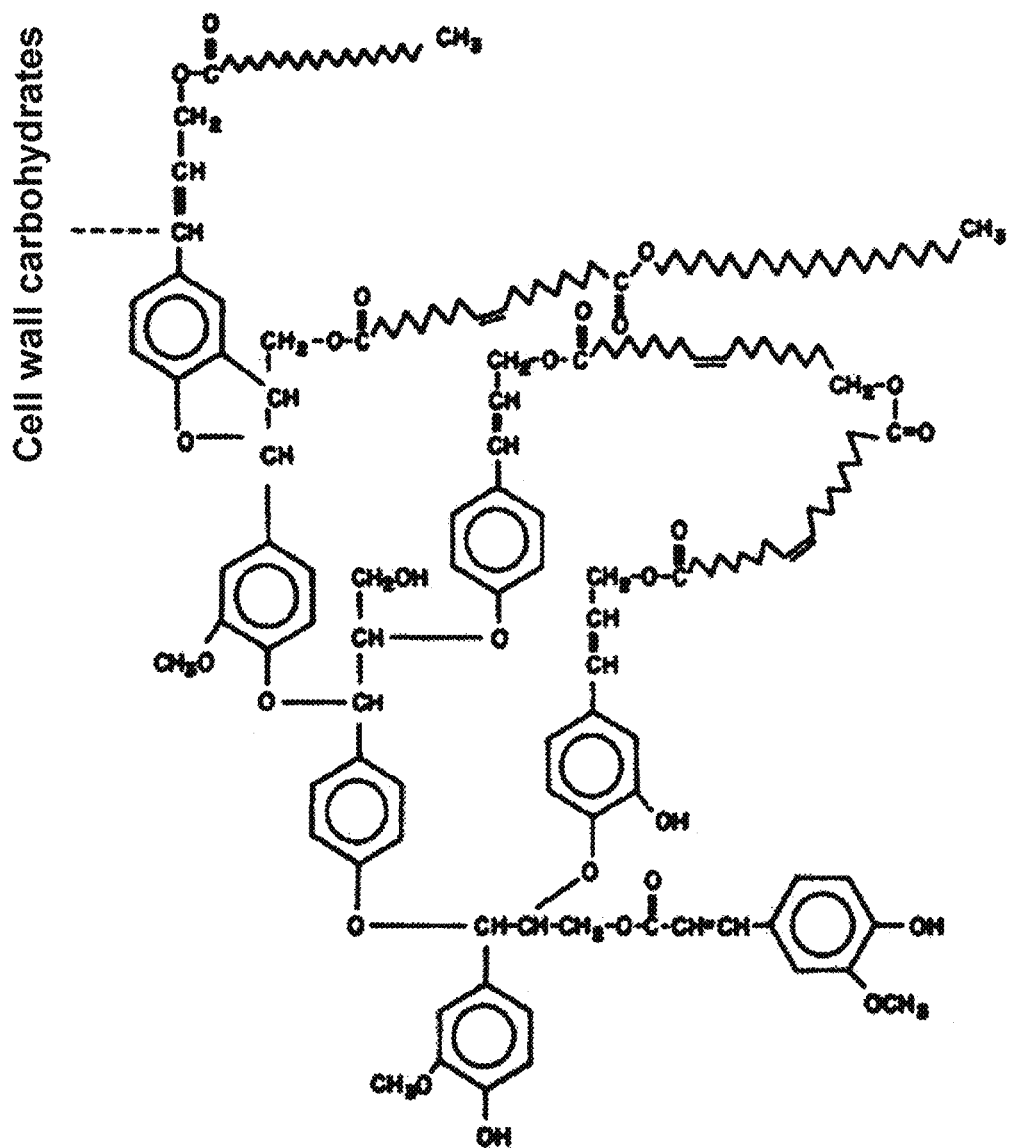
FIG. 3 represents the structure of suberin.
Figure 4:
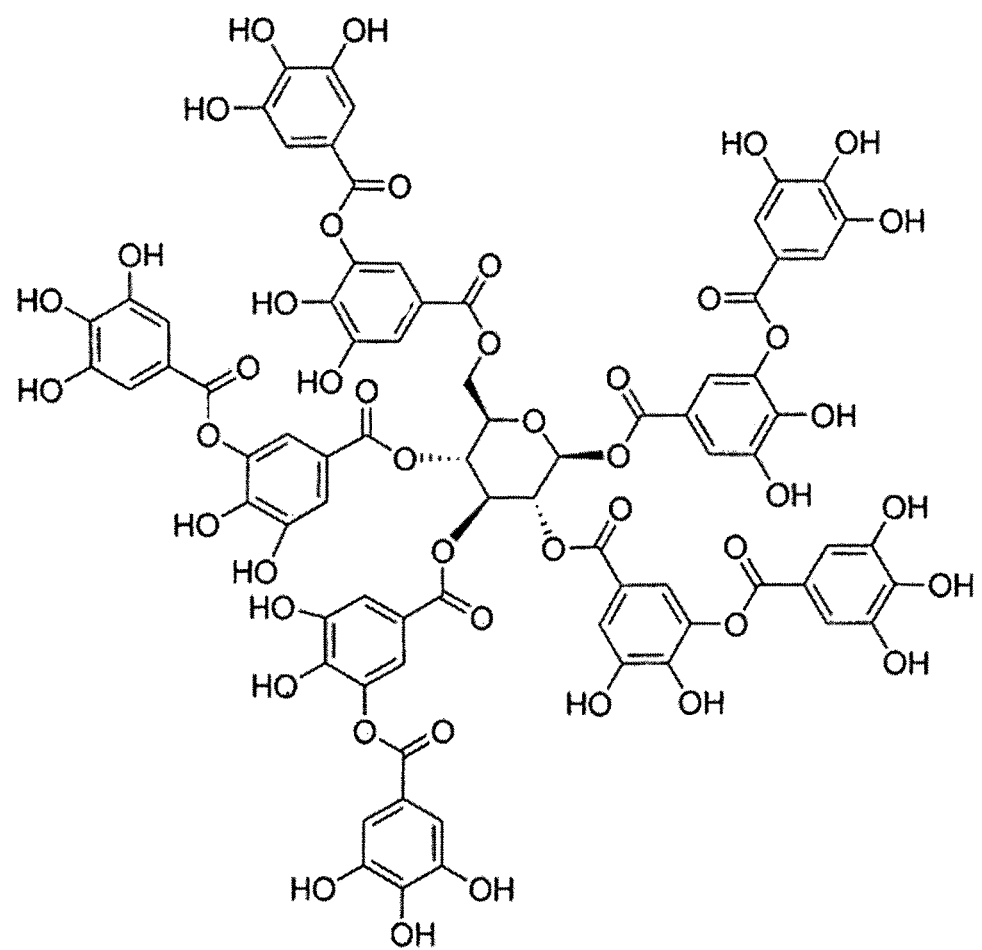
FIG. 4 represents the structure of tannic acid, also known as β-1,2,2,3,6-pentagalloyl-O-D-glucose, and belonging to the category of gallotannins.

The catalytic depolymerization reactions of oxygenated polymer materials according to the invention are presented in FIGS. 1 and 2.

In the examples below, the oxygenated polymers tested are PEG, PET, PC-BPA and PLA. Moreover, the amount of hydrosilane of general formula (I) required to perform the depolymerization is largely dependent on the type of polymer material used and also on the desired compound. Specifically, compounds containing silyl alcohol functions (C—O—$SiR_1R_2R_3$) derived from the depolymerization reaction may be deoxygenated via the same process to lead to C—H bonds.

It should be noted that, by approximation, and so as to calculate the molar yield of the depolymerization reactions, the starting material is considered to consist exclusively of the polymer studied.

The yields obtained are of the order of 30 to 99 mol % relative to the number of mols of starting oxygenated polymer. The conversions were calculated on the basis of the spectroscopic analyses ($^1$H NMR $^{13}$C NMR) using a Brüker DPX 200 MHz spectrometer and via the addition of an internal standard (mesitylene or diphenylmethane). The yields were obtained by means of gas chromatography using as standard the same compound synthesized beforehand (external calibration curve). The mass spectrometry data were acquired on a Shimadzu GCMS-QP2010 Ultra gas chromatograph mass spectrometer machine equipped with a Supelco SLB™-ms molten silica capillary column (30 m×0.25 mm×0.25 μm). The qualitative gas analyses were performed by means of gas chromatography on a Shimadzu GC-2010 machine equipped with a Carboxen™ 1006 PLOT capillary column (30 m×0.53 mm).

General Depolymerization Experimental Protocol

1. Under an inert atmosphere of argon or nitrogen, the hydrosilane of general formula (I), the catalyst (from 1 to 0.001 molar equivalent calculated relative to the number of mols of polymer material initially added) and half the amount of solvent are stirred in a glass container of suitable volume. The concentration of silane in the reaction mixture ranges from 1.0-6.0 mol·$L^{-1}$ (concentration calculated on the basis of half the final volume of solvent introduced).
2. Separately, in a Schlenk tube, the oxygenated polymer material (used as received) is stirred with the remaining half of the solvent.
3. The solution containing the catalyst and the hydrosilane is added slowly (addition time of 5 minutes to 1 hour) by means of a syringe and with stirring, to the Schlenk tube. This tube is left open so as to evacuate the gases produced by the reaction.
4. After the end of addition of the solution and once the evolution of gas has stopped, the Schlenk tube is closed and left stirring. In the case where the starting material is insoluble, the dissolution takes place during the reaction time given that the final products are soluble in the solvents used. Monitoring of the reaction is performed by $^1$H NMR and by GC-MS.
5. Once the reaction is complete (reaction time of 1 minute to 24 hours), the solvent and the volatile compounds are evaporated off by means of a vacuum ramp ($10^{-2}$ mbar). The oil obtained is purified by means of chromatography on silica gel, using an elution gradient from 100:0% to 0:100% of pentane: $CH_2Cl_2$. It should be noted that the liquid products which have low boiling points, such as para-xylene, may be purified by fractional distillation with recycling of the solvent.
6. In the case of products bearing siloxy functions (—$SiOR_1R_2R_3$), these products are hydrolyzed using TBAF.3$H_2$O, to give the corresponding hydrolyzed product. The hydrolysis reaction lasts from 1 minute to 16 hours. The final product is obtained after purification on a chromatography column using an elution gradient from 100:0% to 0:100% of $CH_2Cl_2$:EtOAc.

A set of results is presented below, giving examples of depolymerization of synthetic and biosourced oxygenated polymer materials.

The catalysts tested are $B(C_6F_5)_3$, $(Ph_3)C^+B(C_6F_5)_3^-$ and also the iridium complex ([(POCOP)Ir(H)(acetone)]$^+$B($C_6F_5$)$_4^-$).

The hydrosilanes used are $Et_3SiH$, TMDS and PMHS. The oxygenated polymer materials used are PLA, PEG, PC-BPA, PET, suberin and tannic acid. Suberin is obtained from cork stoppers used in commercial wine bottles. The tannic acid used is extracted from Chinese gall nut extracts. The PET used is a commercial PET taken from Perrier bottles.

A) Depolymerization of Oxygenated Polymers in Presence of $B(C_6F_5)_3$

Example 1

Depolymerization of PC-BPA with Triethylsilane ($Et_3SiH$)

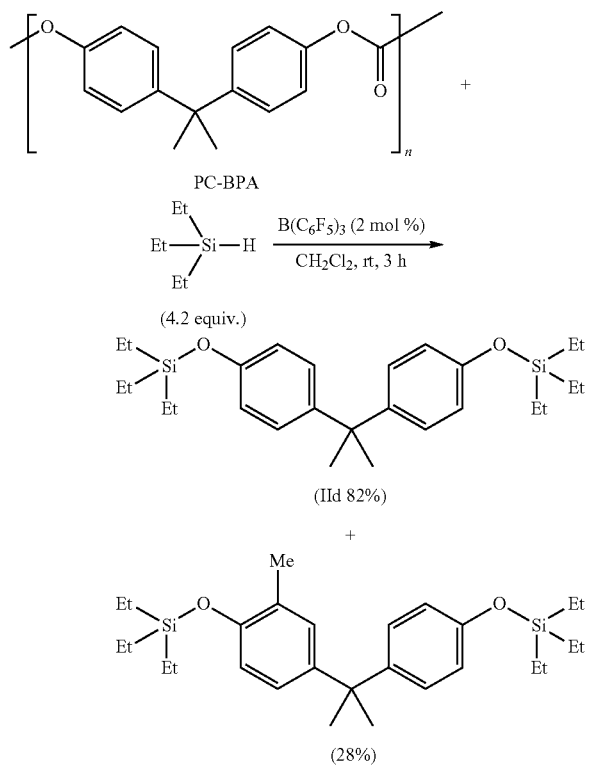

Commercial PC-BPA (123.2 mg, 0.5 mmol, 1 equiv.) was added to 1.5 mL of $CH_2Cl_2$. Separately, $B(C_6F_5)_3$ (5.1 mg, 0.01 mmol, 2 mol %) is dissolved in a mixture of triethylsilane (244.2 mg, 2.1 mmol, 4.2 equiv.) and 1.5 mL of $CH_2Cl_2$. Next, the solution containing the hydrosilane and the catalyst is added slowly to the solution containing the polymer stirred beforehand. After reaction for 3 hours at room temperature (20±5° C.), the solvent is evaporated off under vacuum. The product obtained IId is purified using the same conditions as that described in the general procedure. On conclusion of this purification, product IId is obtained in high purity in a yield of 77% relative to the starting material introduced. Finally, the hydrolysis of product IId is performed with stirring at 25° C. for 2 hours in a solution of $TBAF.3H_2O$ (2.1 equiv. relative to the number of mols of IId) in THF (3 mL). The hydrolyzed product (BPA) is obtained in quantitative yield, in the form of a white solid, after purification on a chromatography column using the conditions described in the general procedure.

Example 2

Depolymerization of PET Using Triethylsilane ($Et_3SiH$)

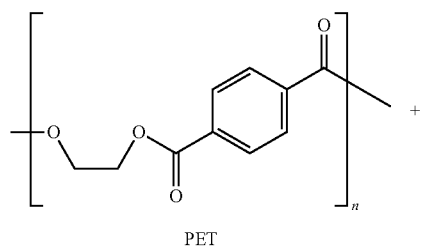

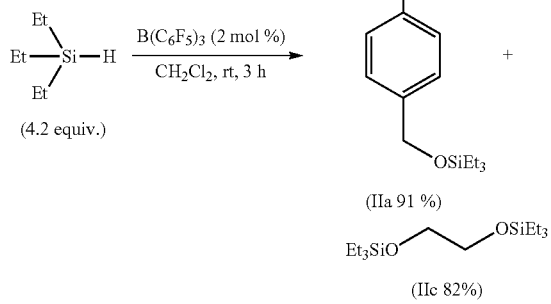

The same procedure using for the depolymerization of PC-BPA with $Et_3SiH$ is used for the depolymerization of PET. In this case, (96.1 mg, 0.5 mmol, 1 equiv.) of PET are used with (244.2 mg, 2.1 mmol, 4.2 equiv.) of triethylsilane and (5 mg, 0.01 mmol, 2 mol %) of $B(C_6F_5)_3$. After reaction for 3 hours at room temperature (20±5° C.), the conversion is total into IIa and IIc. Purification of the products is performed according to the same procedure described in example 1. Hydrolysis of these compounds under the conditions of example 1 leads to the production of ethylene glycol (colorless oil, 72% yield) and 1,4-phenylenedimethanol (white solid, 85% yield).

Example 3

Depolymerization of PET with Polymethylhydrosiloxane (PMHS)

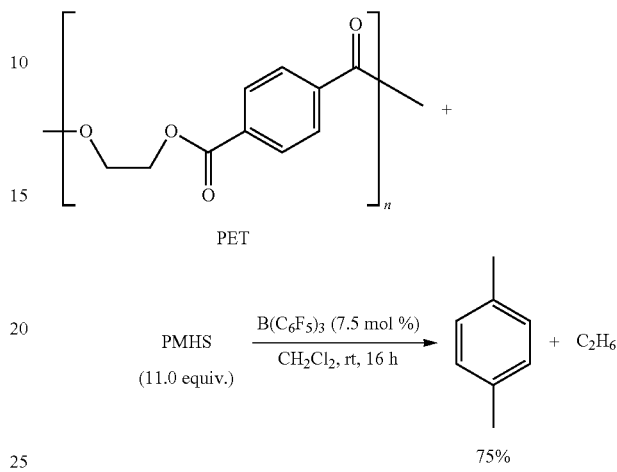

The same procedure as that of example 2 is used for the depolymerization of PET with PMHS. However, the products obtained are ethane and paraxylene. In this case, 96.1 mg (0.5 mmol, 1 equiv.) of PET are used with 330.7 mg (5.5 mmol, 11 equiv.) of PMHS, 19.2 mg (0.04 mmol, 7.5 mol %) of $B(C_6F_5)_3$ and 6 mL of $CH_2Cl_2$. After reaction for 16 hours, the yield of paraxylene obtained is 75%.

Example 4

Depolymerization of PET with Tetramethyldisiloxane (TMDS)

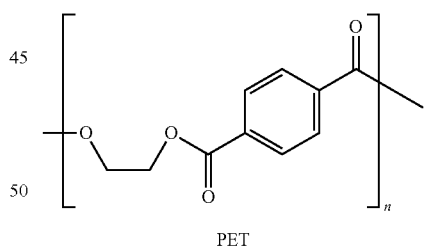

The same procedure as that of example 3 is used for the depolymerization of PET with TMDS. The products obtained are ethane and paraxylene. 96.1 mg (0.5 mmol, 1 equiv.) of PET were used with 400.0 mg (3.0 mmol, 6 equiv.) of TMDS, 12.8 mg (0.025 mmol, 5 mol %) of $B(C_6F_5)_3$ and 3 mL of $CH_2Cl_2$. After reaction for 16 hours, the conversion is total and the yield of paraxylene obtained is 82%.

Example 5

Depolymerization of PLA Using Triethylsilane ($Et_3SiH$)

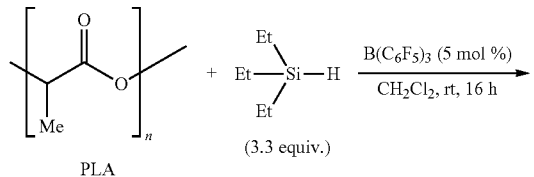

(3.3 equiv.)

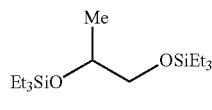

IIb 65%

The same procedure as that of example 2 is used for the depolymerization of PLA with $Et_3SiH$. Product IIb is obtained. In this case, 360.3 mg (0.5 mmol, 1 equiv.) of PLA are used with 191.9 mg (1.7 mmol, 3.3 equiv.) of $Et_3SiH$, 12.8 mg (0.025 mmol, 5 mol %) of $B(C_6F_5)_3$ and 3 mL of $CH_2Cl_2$. After reaction for 3 hours, the yield of product IIb is 65%.

Example 6

Depolymerization of PLA with Polymethylhydrosiloxane (PMHS)

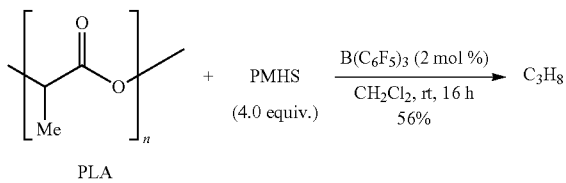

The same procedure as that of example 5 is used for the depolymerization of PLA with PMHS. The product obtained is propane and the solvent used is benzene. In this case, 360.3 mg (0.5 mmol, 1 equiv.) of PLA are used with 120.3 mg (2.0 mmol, 4 equiv.) of PMHS, 5.1 mg (0.01 mmol, 2 mol %) of $B(C_6F_5)_3$ and 3 mL of benzene. After reaction for 16 hours, the conversion is 56%.

It should be noted that the use of $CH_2Cl_2$ as reaction solvent leads to the direct formation of a gel.

Example 7

Depolymerization of PLA with Tetramethyldisiloxane (TMDS)

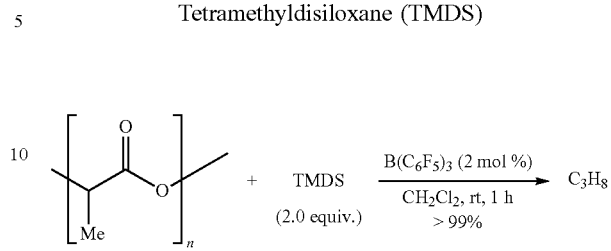

The same procedure as that of example 6 is used for the depolymerization of PLA with TMDS. The reaction takes place in $CH_2Cl_2$. In this case, 360.3 mg (0.5 mmol, 1 equiv.) of PLA are used with 133.3 mg (1.0 mmol, 2 equiv.) of TMDS, 5.1 mg (0.01 mmol, 2 mol %) of $B(C_6F_5)_3$ and 3 mL of $CH_2Cl_2$. After 1 hour of reaction, the conversion is >99%.

Example 8

Depolymerization of Gallotannin with Triethylsilane ($Et_3SiH$)

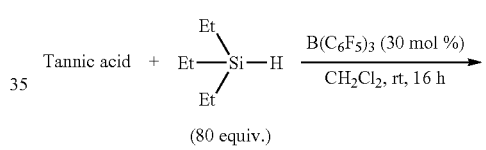

(80 equiv.)

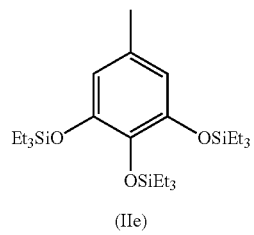

(IIe)

The same procedure as that of example 1 is used for the depolymerization of tannic acid with triethylsilane. In this case, 170.1 mg (0.1 mmol, 1 equiv.) of tannic acid ($C_{76}H_{52}O_{46}$) are used with 930.2 mg (8.0 mmol, 80 equiv.) of $Et_3SiH$, 15.4 mg (0.03 mmol, 30 mol %) of $B(C_6F_5)_3$ and 3 mL of $CH_2Cl_2$ (conditions not optimized). After 16 hours of reaction, the molar yield of product IIe is 132%, i.e. 0.13 mmol. Purification of the product is performed using the same conditions as that described in the general procedure.

It should be noted that the hydrolysis of the product is performed under conditions virtually similar to those described in the general procedure. Specifically, this last step must be performed under an inert atmosphere of argon or nitrogen, given that the product 5-methylbenzene-1,2,3-triol oxidizes directly to quinone in the presence of oxygen.

Example 9

Depolymerization of a PET+PS Mixture with Triethylsilane (Et₃SiH)

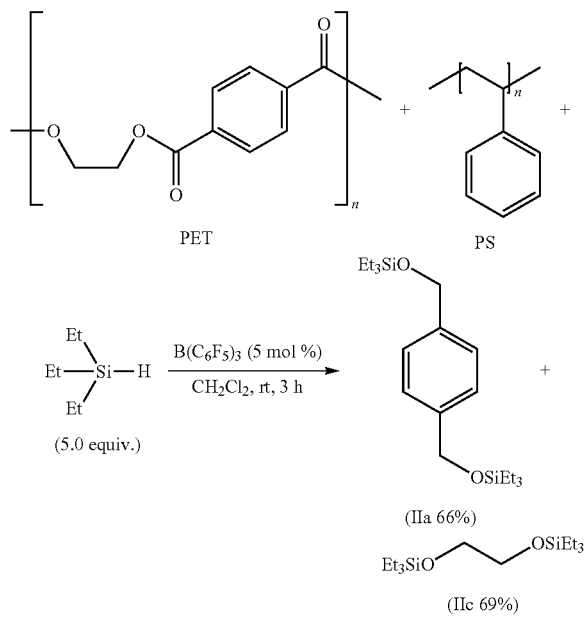

(IIa 66%)

(IIc 69%)

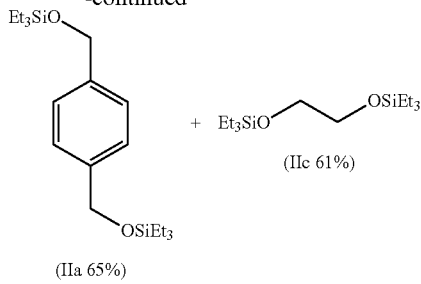

(IIa 65%)

(IIc 61%)

The same procedure as that of example 2 is used for the depolymerization of the PET+PS mixture. In this case, 96.1 mg (0.5 mmol, 1 equiv.) of PET are used with 52.1 mg (0.5 mmol, 1 equiv.) of PS (commercial expanded polystyrene), 290.7 mg (2.5 mmol, 5.0 equiv.) of triethylsilane and 12.8 mg (0.03 mmol, 5 mol %) of B(C₆F₅)₃ in 3 mL of CH₂Cl₂. After reaction for 3 hours, the conversion is total into the products IIa and IIc, PS not having undergone any depolymerization under these conditions. Purification of the products is performed by following the same procedure as that described in example 2. Hydrolysis of these compounds leads to the production of ethylene glycol and 1,4-phenylenedimethanol.

Example 10

Depolymerization of a PET+PVC+PS Mixture with Triethylsilane (Et₃SiH)

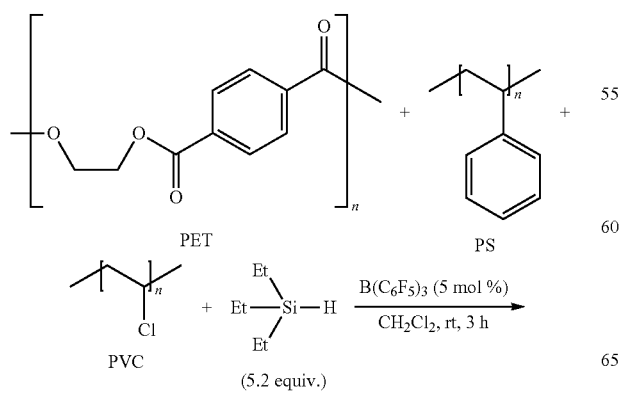

The same procedure as that of example 9 is used for the depolymerization of the PET+PS+PVC mixture. The same amounts of PET and PS are used and 31.3 mg (0.5 mmol, 1 equiv.) of PVC (derived from plumbing pipes) are used in the reaction. Only PET is selectively depolymerized, whereas PVC and PS are not depolymerized under these conditions.

Example 11

Selective Depolymerization of PET in a PET+PLA Mixture with Triethylsilane (Et₃SiH)

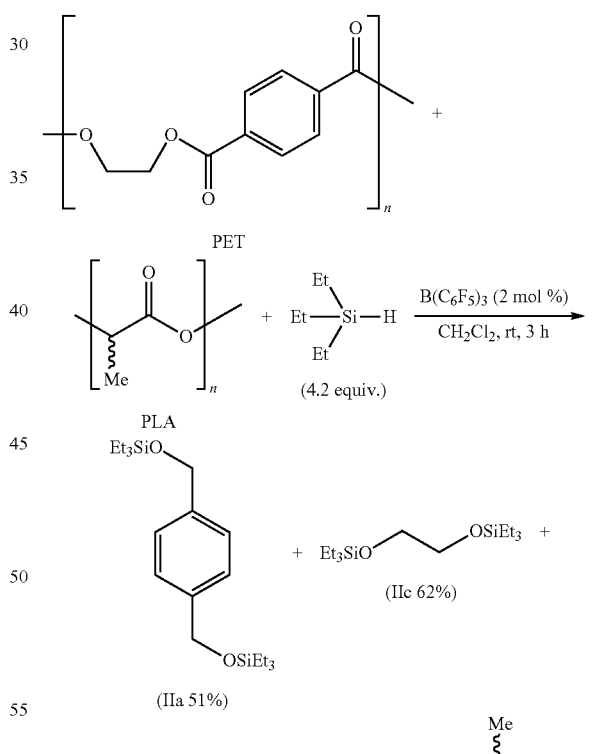

(IIa 51%)

(IIc 62%)

(IIb 0%)

The same procedure as that of example 10 is used for the depolymerization of the PET+PLA mixture. In this case, 96.1 mg (0.5 mmol, 1 equiv.) of PET are used with 360.3 mg (0.5 mmol, 1 equiv.) of PLA, 244.2 mg (2.1 mmol, 4.2 equiv.) of triethylsilane and 5.1 mg (0.01 mmol, 2 mol %) of B(C₆F₅)₃ in 3 mL of CH₂Cl₂. After reaction for 3 hours, products IIa and IIc are obtained. No product derived from the depolymerization of PLA is observed. Purification of the products takes place by following the same procedure as that described in example 2. Hydrolysis of these compounds leads to the production of ethylene glycol and 1,4-phenylenedimethanol.

Example 12

Depolymerization of a PET+PLA Mixture with Triethylsilane (Et₃SiH)

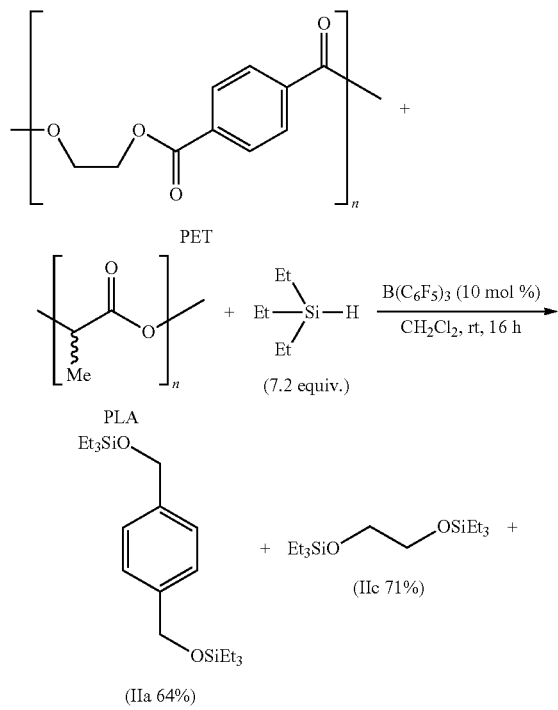

The same procedure as that of example 11 is used for the depolymerization of the PET+PLA mixture. However, the amount of hydrosilane used is 418.6 mg (3.6 mmol, 7.2 equiv.) and the amount of catalyst used is 25.6 mg (0.06 mmol, 10 mol %). After reaction for 16 hours, products IIa, IIb and IIc are obtained. Hydrolysis of these compounds leads to the production of ethylene glycol, 1,2-propanediol and 1,4-phenylenedimethanol.

Example 13

Depolymerization of Suberin Derived from Cork with Triethylsilane (Et₃SiH)

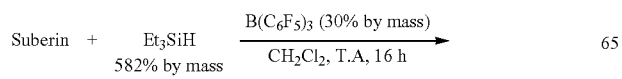

-continued

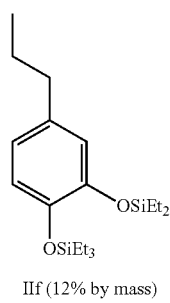

IIf (12% by mass)

In order to test the possibility of depolymerization of suberin by hydrosilylation with B(C₆F₅)₃, cork derived from wine bottle stoppers was finely ground and then dried under vacuum overnight. Next, the same procedure as that of example 1 is used for the depolymerization of suberin. In this case, 100.0 mg of cork are used with 582.4 mg (5.0 mmol, 582% by mass) of Et₃SiH, 30 mg (0.59 mmol, 30% by mass) of B(C₆F₅)₃ and 3 mL of CH₂Cl₂ (conditions not optimized). After reaction for 16 hours at room temperature (20±5° C.), a large amount of the initially insoluble solid is dissolved. GC-MS analysis of the reaction residue shows the presence of a complex mixture of several products, among which product IIf was able to be identified and quantified at 12% by mass relative to the mass of cork initially introduced.

B) Depolymerization of Oxygenated Polymers in the Presence of (Ph₃)C⁺B(C₆F₅)₃⁻

Example 14

Depolymerization of PC-BPA Using (Ph₃)C⁺B(C₆F₅)₃⁻

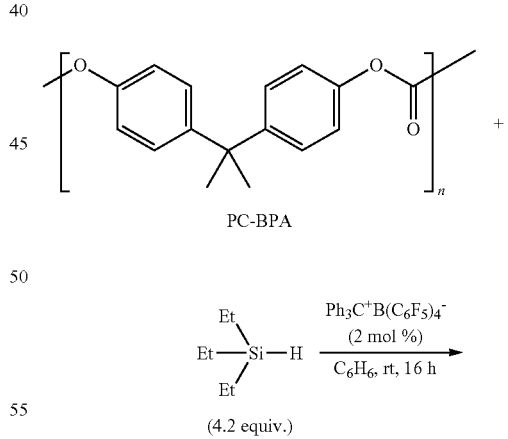

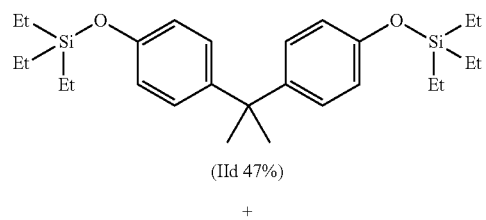

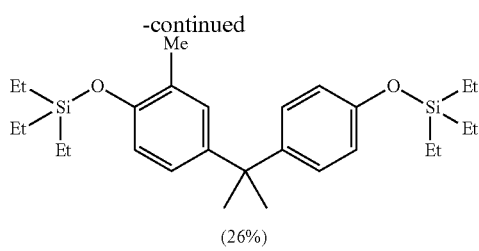

(26%)

The same procedure as that of example 1 is used for the depolymerization of PC-BPA using $(Ph_3)C^+B(C_6F_5)_3^-$. In this case, 123.2 mg (0.5 mmol, 1 equiv.) of PC-BPA are used with 244.2 mg (2.1 mmol, 4.2 equiv.) of triethylsilane and 9.2 mg (0.01 mmol, 2 mol %) of $(Ph_3)C^+B(C_6F_5)_3^-$ in $C_6H_6$ (3 mL) After reaction for 16 hours, the conversion is total and IId is obtained in a yield of 47%. Purification of the products is performed following the same procedure described in example 1.

C) Depolymerization of Oxygenated Polymers in the Presence of the Iridium Catalyst $([(POCOP)Ir(H)(acetone)]^+B(C_6F_5)_4^-)$ Example 15

Depolymerization of PET Using $([(POCOP)Ir(H)(Acetone)]^+B(C_6F_5)_4^-)$

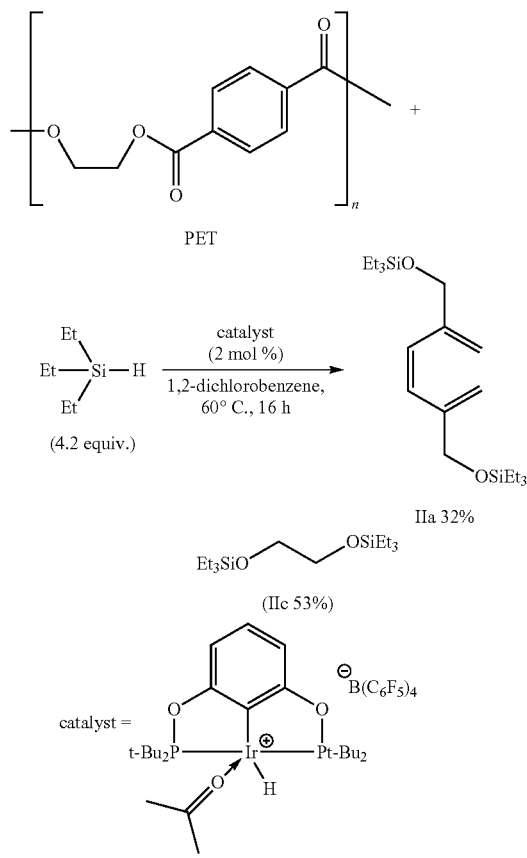

The same procedure used for the depolymerization of PET with $Et_3SiH$ and $B(C_6F_5)_3$ is used for the depolymerization of PET with $Et_3SiH$ and the iridium catalyst ([(PO-COP)Ir(H)(acetone)]$^+$B($C_6F_5$)$_4^-$). In this case, 96.1 mg (0.5 mmol, 1 equiv.) of PET are used with 291.1 mg (2.5 mmol, 5 equiv.) of triethylsilane, 1.5 mL of 1,2-dichlorobenzene and 13.4 mg (0.01 mmol, 2 mol %) of ([(POCOP)Ir(H)(acetone)]$^+$B($C_6F_5$)$_4^-$) After reaction for 16 hours at 60±5° C., products IIa and IIc are produced in respective yields of 32 and 53%. Purification of the products is performed by following the same procedure described in example 2.

Characterization of the Molecules Obtained

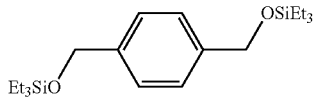

IIa $^1$H NMR (200 MHz, CDCl$_3$, Me$_4$Si) δ (ppm)=7.30 (4H, s, Ar—H), 4.72 (4H, s, CH$_2$—O), 1.05-0.91 (18 H, m, CH$_3$CH$_2$Si), 0.72-0.54 (12 H, m, CH$_3$CH$_2$Si).

$^{13}$C NMR (50 MHz, CDCl$_3$, Me$_4$Si): δ (ppm)=140.2, 126.3, 64.7, 6.9, 4.6.

MS: IE (m/z): 337 (17); 205 (20); 154 (9); 118 (11); 117 (100); 115 (30); 112 (9); 105 (12); 104 (31); 103 (12); 87 (50); 75 (12); 59 (27).

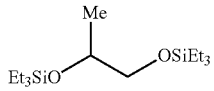

IIb $^1$H NMR (200 MHz, CDCl$_3$, Me$_4$Si) δ (ppm)=3.81 (1H, sex, $^3$J=6.1 Hz, Me-CH), 3.61-3.47 (1H, m, CH$_2$—O), 3.40-3.24 (1H, m, CH$_2$—O), 1.14 (3H, d, $^3$J=6.1 Hz, CH-CH$_3$), 1.04-0.88 (18 H, m, CH$_3$CH$_2$Si), 0.70-0.51 (12 H, m, CH$_3$CH$_2$Si).

$^{13}$C NMR (50 MHz, CDCl$_3$, Me$_4$Si): δ (ppm)=69.3, 68.7, 20.9, 7.0, 6.9, 4.9, 4.5.

MS: IE (m/z): 275 (34); 217 (62); 189 (100); 161 (55); 159 (64); 133 (23); 131 (51); 115 (89); 105 (21); 95 (42); 87 (93); 81 (25); 59 (82).

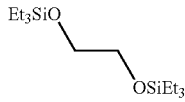

IIc $^1$H NMR (200 MHz, CDCl$_3$, Me$_4$Si) δ (ppm)=3.67 (4H, s, O-CH$_2$), 1.05-0.87 (18 H, m, CH$_3$CH$_2$Si), 0.70-0.52 (12 H, m, CH$_3$CH$_2$Si).

$^{13}$C NMR (50 MHz, CDCl$_3$, Me$_4$Si): δ (ppm)=64.3, 6.9, 4.5.

MS: IE (m/z): 262 (11); 261 (44); 217 (20); 190 (13); 189 (66); 161 (28); 117 (11); 115 (65); 88 (37); 87 (100); 74 (14); 59 (56); 58 (12).

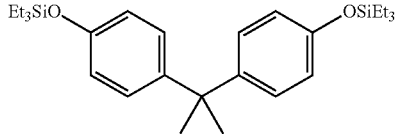

IId

¹H NMR (200 MHz, CDCl₃, Me₄Si) δ (ppm)=6.95 (4H, d, ³J=8.6 Hz, Ar—H), 6.62 (4H, d, ³J=8.6 Hz, Ar—H), 1.51 (6H, s, CH₃—Cq), 0.97-0.79 (18 H, m, CH₃CH₂Si), 0.71-0.52 (12 H, m, CH₃CH₂Si).

¹³C NMR (50 MHz, CDCl₃, Me₄Si): δ (ppm)=153.3, 143.8, 127.8, 119.2, 41.4, 31.2, 6.8, 5.1.

MS: IE (m/z): 456 (13); 443 (14); 442 (37); 441 (59); 249 (22); 221 (11); 199 (17); 143 (13); 115 (15); 96 (12); 87 (100); 82 (10); 59 (52).

IIe

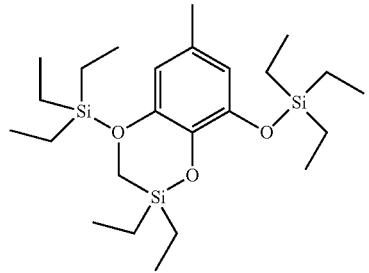

¹H NMR (200 MHz, CDCl₃, Me₄Si) δ (ppm)=6.25 (2H, s, Ar—H), 2.16 (3H, s, Ar—CH₃), 1.10-0.85 (27 H, m, CH₃CH₂Si), 0.84-0.59 (18 H, m, CH₃CH₂Si).

¹³C NMR (50 MHz, CDCl₃, Me₄Si): δ (ppm)=147.9, 136.4, 129.6, 114.2, 21.3, 7.0, 6.8, 5.4, 5.2.

MS: IE (m/z): 483 (5); 310 (7); 309 (26); 147 (5); 116 (7); 115 (66); 88 (9); 87 (100); 86 (4); 60 (5); 59 (56); 58 (5); 32 (5).

IIf

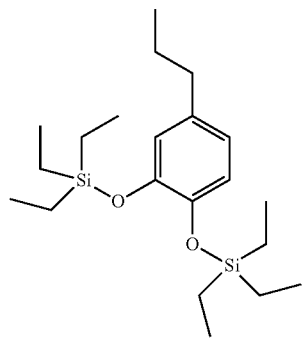

¹H NMR (200 MHz, CDCl₃, Me₄Si) δ (ppm)=6.71 (1 H, d, ³J=8.1 Hz, Ar—H), 6.63 (1 H, s, Ar—H), 6.58 (1 H, d, ³J=8.1 Hz, Ar—H), 2.45 (2 H, t, ³J=7.8 Hz, Ar—CH₂), 1.57 (2 H, sex, ³J=7.8 Hz, CH₂—CH₃), 0.98 (18 H, t, ³J=7.9 Hz, CH₃CH₂Si), 0.90 (3 H, t, ³J=7.8 Hz, CH₃CH₂Si), 0.74 (12 H, q, ³J=7.9 Hz, CH₃CH₂Si).

¹³C NMR (50 MHz, CDCl₃, Me₄Si): δ (ppm)=146.5, 144.7, 136.0, 121.3, 120.9, 120.2, 37.4, 24.7, 13.9, 6.9, 5.3, 5.2.

MS: IE (m/z): 380 (9); 351 (4); 207 (8): 117 (4): 116 (11): 115 (100): 88 (7): 87 (74); 59 (45); 58 (4).

Example 16

Process for Preparing Aromatic Compounds Comprising a Step of Depolymerization of PET Using Triethylsilane (Et₃SiH)/Recycling of a Plastic Material Waste commercial plastic soda bottles are collected and the bottles made of PET are sorted and isolated. They are then ground and grated manually to a powder.

The PET powder is then depolymerized under the conditions of example 2.

Finally, hydrolysis of products IIa and IIb is performed by stirring the mixture at 25° C. for 2 hours in a solution of TBAF.3H₂O (2.1 equiv. relative to the number of mols of IIa and IIb, taken together) in THF (3 mL). The hydrolyzed products are then separated by distillation under reduced pressure and purification on a chromatography column. This procedure leads to the production of ethylene glycol (colorless oil, 72% yield) and 1,4-phenylenedimethanol (white solid, 85% yield).

Abbreviations Used:
BHET=bis(hydroxyethylene) terephthalate
BPA=bisphenol A
DMC=dimethyl carbonate
EG=ethylene glycol
PC-BPA=carbonate polymer of bisphenol A
PET=polyethylene terephthalate
PLA=polylactic acid
PLLA=Poly(L-lactide)
PS=polystyrene
PVC=polyvinyl chloride
TBAF=Tetra-n-butylammonium fluoride
TBD=Triazabicyclodecene or 1,5,7-triazabicyclo[4.4.0]dec-5-ene
TEG=triethylene glycol
TPA=terephthalic acid

The invention claimed is:

1. A process for depolymerizing oxygenated polymer materials by selective cleavage of the oxygen-carbonyl bonds of the ester functions and of the carbonate functions, comprising a step of placing said oxygenated polymer materials in contact with a silane compound of formula (I)

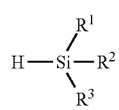 (I)

in which
R¹, R² and R³ represent, independently of each other, a hydrogen atom, a halogen atom, a hydroxyl group, an alkyl group, an alkenyl group, an alkynyl group, an alkoxy group, an aryloxy group, a silyl group, a siloxy group, an aryl group, an amino group, said alkyl, alkenyl, alkynyl, alkoxy, silyl, siloxy, aryl and amino groups being optionally substituted, or R¹ is as defined above and R² and R³, taken together with the silicon atom to which they are linked, form an optionally substituted silyl heterocycle;

in the presence of a catalyst which is:
an organic catalyst selected from the group consisting of
the carbocations of formula $(X^1)_3C^+$ with $X^1$ representing a hydrogen atom, an alkyl group, an aryl group, an alkoxy group, a silyl group, a siloxy group and a halogen atom;
oxoniums chosen from $(CH_3)_3O^+BF_4^-$ and $(CH_3CH_2)_3O^{+BF_4^-}$;
a silylium ion $(R^5)_3Si^+$ with $R^5$ representing, independently of each other, a hydrogen atom, an alkyl group, an alkenyl group, an alkynyl group, an aryl group, a heteroaryl group, a heterocycle, a silyl group, a siloxy group;
disilyl cations;
with the anionic counterion of said silylium ion, of said carbocations and of said disilyl cations being
a halide selected from the group consisting of F⁻, Cl⁻, Br⁻ and I⁻; or
an anion selected from the group consisting of $BF_4^-$, $SbF_6^-$, $B(C_6F_5)_4^-$, $B(C_6H_5)_4^-$, $CF_3SO_3^-$, $PF_6^-$; or
an organometallic catalyst comprising ruthenium or iridium selected from the group consisting of:
the iridium complexes of formula (II):

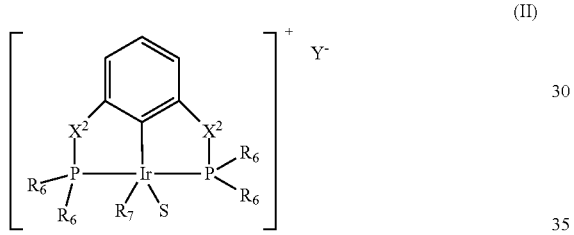

(II)

in which
$R^6$ represents an alkyl or aryl group;
$R^7$ represents a hydrogen atom or an alkyl group;
$X^2$ represents a —$CH_2^-$ group or an oxygen atom;
Y⁻ represents a counterion selected from the group consisting of $B(C_6F_5)_4^-$ and $B(C_6H_5)_4^-$; and
S represents a solvent molecule, coordinated to the complex, selected from the group consisting of dimethyl sulfoxide (DMSO), acetonitrile ($CH_3CN$) and acetone ($CH_3COCH_3$); and
the ruthenium complexes of formula (III):

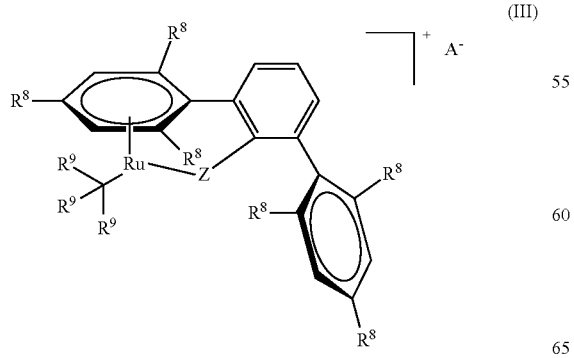

(III)

in which
$R^8$ represents a hydrogen atom or an alkyl group;
$R^9$ represents an aryl or an alkyl group, said aryl and alkyl groups being optionally substituted;
Z represents a —$CH_2^-$ group, an oxygen atom or a sulfur atom; and
A⁻ represents a counterion chosen from $B(C_6F_5)_4^-$ and $[CHB_{11}H_5Cl_6]^-$; or
a catalyst of Lewis acid type selected from the group consisting of:
the boron compound selected from the group consisting of $BF_3$, $BF_3(Et_2O)$, $BCl_3$, $BBr_3$, triphenylhydroborane, tricyclohexylhydroborane, $B(C_6F_5)_3$, B-methoxy-9borabicyclo[3.3.1]nonane (B-methoxy-9-BBN), B-benzyl-9-borabicyclo[3.3.1]nonane (B-benzyl-9-BBN);
the borenium compound Me-TBD-BBN[30], the borenium ferrocene derivatives corresponding to the formula

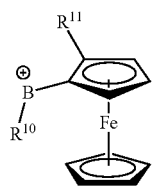

borenium ferrocene in which $R^{10}$=phenyl and $R^{11}$ =3,5-dimethylpyridyl;
aluminum compounds selected from the group consisting of $AlCl_3$, $AlBr_3$, aluminum isopropoxide (Al(O-i-Pr)₃), aluminum ethoxide ($Al(C_2H_3O_2)$), Krossing's salt $[Aq(CH_2Cl_2)]\{Al\,[OC(CF_3)_3]_4\}$, the Li$\{Al\,[OC(CF_3)_3]_4\}$, $Et_2Al^+$;
indium compounds chosen from $InCl_3$, $In(OTf)_3$;
iron compounds chosen from $FeCl_3$, $Fe(OTf)_3$
tin compounds chosen from $SnCl_4$, $Sn(OTf)_2$,
phosphorus compounds chosen from $PCl_3$, $PCl_5$, $POCl_3$
trifluoromethanesulfonate or triflate compounds ($CF_3SO_3^-$) of transition metals and of lanthanides chosen from scandium triflate, ytterbium triflate, yttrium triflate, cerium triflate, samarium triflate and neodymium triflate.

2. The process as claimed in claim 1, wherein the oxygenated polymers are selected from the group consisting of:
saturated or unsaturated polyesters selected from the group consisting of polyglycolic acid (PGA), polylactic acid (PLA), polycaprolactone (PCL), polyhydroxyalkanoate (PHA), polyhydroxybutyrate (P3HB), polyhydroxyvalerate (PHV), polyethylene adipate (PEA), polybutylene succinate (PBS), poly(3-hydroxybutyrate-co-3-hydroxyvalerate (PHBV), polyethylene terephthalate (PET), polybutylene terephthalate (PBT), polytrimethylene terephthalate (PTT), polyethylene naphthalate (PEN),
polycarbonates selected from the group consisting of PC-BPA, polypropylene carbonate (PPC), polyethylene carbonate (PEC), poly(hexamethylene carbonate), allyl diglycol carbonate (ADC) or CR 39, and
hydrolyzable tannins, especially gallotannins and ellagitannins, and suberin.

3. The process as claimed in claim 1, wherein the oxygenated polymers are selected from the group consisting of:

PET and PLA;

PC-BPA;

gallotannins and ellagitannins, and suberin.

4. The process as claimed in claim 1, wherein the catalyst is an organic catalyst selected from the group consisting of:

carbocations selected from the group consisting of the trityl cation $((C_6H_5)_3C^+)$, tropilium $(C_7H_7)^+$, the benzilic cation $(C_6H_5CH_2^+)$, the allylic cation $(CH_3—CH^+—CH=CH_2)$, methylium $(CH_3^+)$, cyclopropylium $(C_3H_5^+)$, the cyclopropyl carbocation selected from the group consisting of the dimethylcyclopropyl carbocation and the dicyclopropyl carbocation, the triazabicyclodecene (TBD) cation, acylium $(R^1—C=O)^+$ with $R^1$ as defined above and selected from the group consisting of methyl, propyl and benzyl, benzenium $(C_6H_5)^+$, and the norbornyl cation $(C_7H_{11})^+$;

oxoniums selected from the group consisting of $(CH_3)_3O^+BF_4^-$ and $(CH_3CH_2)_3O^+BF_4^-$;

a silylium ion selected from the group consisting of $Et_3Si^+$ and $Me_3Si^+$;

disilyl cations bearing a bridging hydride selected from the group consisting of the formulae indicated below

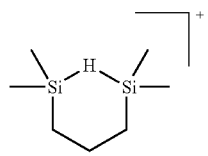
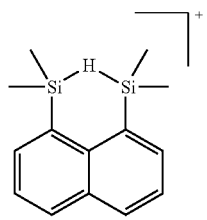

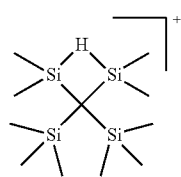
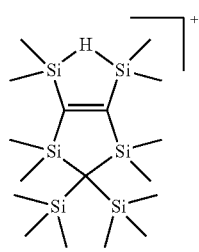

with the anionic counterion of said silylium ion, of said carbocations and of said disilyl cations being a halide selected from the group consisting of $F^-$, $Cl^-$, $Br^-$ and $I^-$; or an anion selected from the group consisting of $BF_4^-$, $SbF_6^-$, $B(C_6F_5)_4^-$, $B(C_6H_5)_4^-$, $CF_3SO_3^-$, $PF_6^-$.

5. The process as claimed in claim 4, wherein the organic catalyst is selected from the group consisting of triphenylcarbenium tetrakis(perfluorophenyl)borate $[(Ph)_3C^+ B(C_6F_5)_4]^-$.

6. The process as claimed in claim 1, wherein the catalyst is an organometallic catalyst selected from the group consisting of:

the iridium complexes of formula (II):

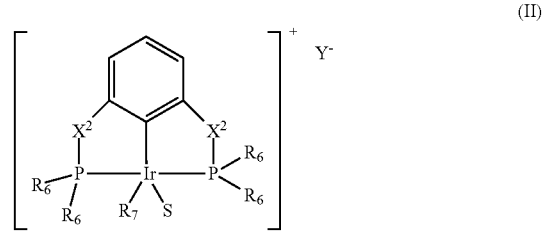

in which $R^6$ represents an alkyl or aryl group;
$R^7$ represents a hydrogen atom or an alkyl group;
$X^2$ represents a $—CH_2^{31}$ group or an oxygen atom;
$Y^-$ represents a counterion selected from the group consisting of $B(C_6F_5)_4^-$ and $B(C_6H_5)_4$; and
S represents a solvent molecule, coordinated to the complex, selected from the group consisting of dimethyl sulfoxide (DMSO), acetonitrile $(CH_3CN)$ and acetone $(CH_3COCH_3)$; and the ruthenium complexes of formula (III):

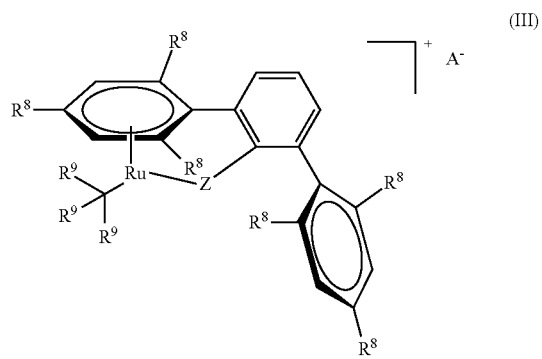

in which $R^8$ represents a hydrogen atom or an alkyl group;
$R^9$ represents an aryl or an alkyl group, said aryl and alkyl groups being optionally substituted;
Z represents a $—CH_2^-$ group, an oxygen atom or a sulfur atom; and
$A^-$ represents a counterion selected from the group consisting of $B(C_6F_5)_4^-$ and $[CHB_{11}H_5Cl_6]^-$.

7. The process as claimed in claim 1, wherein the organometallic catalyst is selected from the group consisting of:

the iridium complex [(POCOP)Ir(H)(acetone)]+ $B(C_6F_5)_4^-$ with (POCOP) representing 2,6-bis(di-tert-butylphosphinito)phenyl; and the ruthenium complex of formula (III) in which
$R^8$ represents a methyl group;
$R^9$ represents p-$FC_6H_4$;
Z represents a sulfur atom; and
A- represents $B(C_6F_5)_4^-$.

8. The process as claimed in claim 1, wherein the catalyst is a catalyst of Lewis acid type selected from the group consisting of:

the boron compound selected from the group consisting of $BF_3$, $BF_3(Et_2O)$, $BCl_3$, $BBr_3$, triphenylhydroborane, tricyclohexylhydroborane, $B(C_6F_5)_3$, B-methoxy-9-borabicyclo[3.3.1]nonane (B-methoxy-9-BBN), B-benzyl-9-borabicyclo[3.3.1]nonane (B-benzyl-9-BBN);

the borenium compound Me-TBD-BBN⁺, the borenium ferrocene derivatives corresponding to the formula

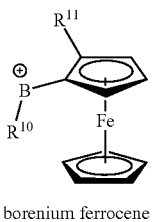

borenium ferrocene in which $R^{10}$=phenyl and $R^{11}$=3,5-dimethylpyridyl;
aluminum compounds selected from the group consisting of $AlCl_3$, $AlBr_3$, aluminum isopropoxide ($Al(O-i-Pr)_3$), aluminum ethoxide ($Al(C_2H_3O_2)$), Krossing's salt [Ag($CH_2Cl_2$)]{Al[OC(CF_3)_3]_4}, the Li{Al[OC(CF_3)_3]_4}, $Et_2Al^+$;
indium compounds selected from the group consisting of $InCl_3$, $In(OTf)_3$;
iron compounds selected from the group consisting of $FeCl_3$, $Fe(OTf)_3$;
tin compounds selected from the group consisting of $SnCl_4$, $Sn(OTf)_2$;
phosphorus compounds selected from the group consisting of $PCl_3$, $PCl_5$, $POCl_3$;
trifluoromethanesulfonate or triflate compounds ($CF_3SO_3^-$) of transition metals and of lanthanides selected from the group consisting of scandium triflate, ytterbium triflate, yttrium triflate, cerium triflate, samarium triflate and neodymium triflate.

9. The process as claimed in claim 1, wherein the catalyst of Lewis acid type is selected from the group consisting of $BF_3$; $InCl_3$; the borenium ferrocene derivative in which $R^{10}$=phenyl and $R^{11}$=3,5-dimethylpyridyl.

10. The process as claimed in claim 1, wherein the silane compound used is a silane compound of formula (I) in which $R^1$, $R^2$ and $R^3$ represent, independently of each other, a hydrogen atom, a hydroxyl group; an alkyl group selected from the group consisting of methyl, ethyl, propyl, butyl, and branched isomers thereof; an alkoxy group whose alkyl radical is selected from the group consisting of methyl, ethyl, propyl, butyl and branched isomers thereof; an aryl group selected from the group consisting of phenyl and benzyl; an aryloxy group whose aryl radical is selected from the group consisting of phenyl and benzyl; a siloxy group (—O—Si(X)₃) in which each X, independently of each other, is selected from the group consisting of a hydrogen atom, an alkyl group selected from the group consisting of methyl, ethyl, propyl, an aryl group selected from the group consisting of phenyl and benzyl, a polymeric organosilane of general formula

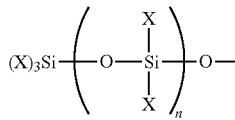

in which X is as defined above and n is an integer between 1 and 20 000; said alkyl, alkoxy, aryl, aryloxy, siloxy and aryl groups being optionally substituted.

11. The process as claimed in claim 10, wherein n is an integer between 1 and 5000.

12. The process as claimed in claim 10, wherein n is an integer between 1 and 1000.

13. The process as claimed in claim 1, wherein the silane compound used is a silane compound of formula (I) in which $R^1$, $R^2$ and $R^3$ represent, independently of each other, a hydrogen atom; an alkyl group selected from the group consisting of methyl, ethyl, propyl and the branched isomer thereof; an aryl group selected from the group consisting of benzyl and phenyl; a siloxy group selected from the group consisting of polydimethylsiloxane (PDMS), polymethylhydroxysiloxane (PMHS) and tetramethyldisiloxane (TMDS).

14. The process as claimed in claim 1, wherein the depolymerization is performed at a pressure of one or a mixture of inert gases selected from the group consisting of nitrogen and argon, or of gases generated by the process, especially methane and hydrogen.

15. The process as claimed in claim 14, wherein the pressure is between 0.2 and 50 bar, limits inclusive.

16. The process as claimed in claim 1, wherein the depolymerization is performed at a temperature of between 0 and 150° C., limits inclusive.

17. The process as claimed in claim 1, wherein the depolymerization is performed in one or a mixture of at least two solvents selected from the group consisting of:
silyl ethers selected from the group consisting of 1,1,1,3,3,3-hexamethyldisiloxane (($Me_3Si)_2O$), 1,1,1,3,3,3-hexaethyldisiloxane (($Et_3Si)_2O$);
hydrocarbons selected from the group consisting of benzene, toluene, pentane and hexane;
sulfoxides selected from the group consisting of dimethyl sulfoxide (DMSO);
alkyl halides selected from the group consisting of chloroform, methylene chloride, chlorobenzene, dichlorobenzene.

18. The process as claimed in claim 1, wherein the mol ratio between the silane compound of formula (I) and the oxygenated polymer material is between 0.1 and 20, limits inclusive.

19. The process as claimed in claim 1, wherein the amount of catalyst is from 0.001 to 1 molar equivalent, limits inclusive, relative to the initial number of mols of the oxygenated polymer material.

20. A process for recycling plastic materials or mixtures of plastic materials containing at least one oxygenated polymer, wherein it comprises a step of depolymerizing oxygenated polymer materials as claimed in claim 1.

21. A process for preparing mono-, di- and/or tricyclic aromatic compounds in which each ring is optionally mono-, di- and/or trioxygenated, wherein it comprises a step of depolymerizing oxygenated polymer materials as claimed in claim 1.

* * * * *